United States Patent [19]

Trijzelaar et al.

[11] 4,442,106
[45] Apr. 10, 1984

[54] QUINOLINE DERIVATIVES, PHARMACEUTICAL COMPOSITIONS CONTAINING SUCH COMPOUNDS, AND METHODS OF TREATING CARDIOVASCULAR CONDITIONS WITH THEM

[75] Inventors: Hans B. Trijzelaar, Zeist; Ronus de Bode, Bilthoven; Hendricus B. A. Welle, Maarssen, all of Netherlands

[73] Assignee: Acfchemiefarma N.V., Netherlands

[21] Appl. No.: 240,808

[22] Filed: Mar. 5, 1981

[30] Foreign Application Priority Data

Mar. 6, 1980 [NL] Netherlands .................. 8001369

[51] Int. Cl.$^3$ .............. A61K 31/47; C07D 401/06
[52] U.S. Cl. ........................... 424/258; 546/156; 546/157; 546/168; 546/174; 546/176; 546/177
[58] Field of Search ........... 546/156, 157, 176, 177; 424/258

[56] References Cited

U.S. PATENT DOCUMENTS

| | | | |
|---|---|---|---|
| 3,914,235 | 10/1975 | Gutzwiller et al. | 424/258 X |
| 3,953,453 | 4/1976 | Grethe et al. | 546/134 |
| 4,237,139 | 12/1980 | Champseix et al. | 424/258 |
| 4,238,612 | 12/1980 | Barieux et al. | 546/153 |
| 4,299,835 | 11/1981 | Champseix et al. | 424/258 |
| 4,402,961 | 9/1983 | Dubroeucq et al. | 424/258 |

FOREIGN PATENT DOCUMENTS

| | | |
|---|---|---|
| 2315148 | 10/1973 | Fed. Rep. of Germany . |
| 2206944 | 6/1974 | France .................. 546/176 |

OTHER PUBLICATIONS

Grethe et al., Chemical Abstracts, vol. 83, 114,718j (1975).
Heidelberger et al., J. Am. Chem. Soc., vol. 44, pp. 1098–1107 (1922).
Wirth, Chemical Abstracts, vol. 76, 103776f (1972).
Wirth, Chemical Abstracts, vol. 80, 124762w (1974).
Dawes, British J. Pharmacol., 1, pp. 90–111 (1946).

*Primary Examiner*—Donald G. Daus
*Assistant Examiner*—Diana G. Rivers
*Attorney, Agent, or Firm*—Jacobs & Jacobs

[57] ABSTRACT

The invention is concerned with novel quinoline derivatives having cardiovascular activities of formula 1

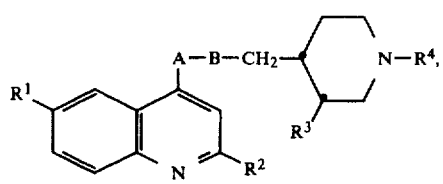

in which A—B is —CH$_2$—CH$_2$—, —CHOH—CH$_2$, —CH$_2$—CHOH—, —C(O)—CH$_2$—, —CH$_2$—C(O)—, —C(NOR$^5$)—CH$_2$— or —CH$_2$—C(NOR$^5$)—; R$^1$ is hydrogen, hydroxy or lower alkoxy; R$^2$ is lower alkyl, hydroxy, lower alkoxy or CF$_3$; R$^3$ is ethyl or vinyl; R$^4$ is C$_{1-9}$ alkyl, C$_{2-9}$ hydroxyalkyl or lower alkoxyalkyl, C$_{5-6}$ cycloalkyl, C$_{3-6}$ cycloalkyl lower alkyl, cyano lower alkyl, lower alkenyl, lower alkynyl, tetrahydrofurfuryl, mono- or di-lower alkylamino lower alkyl; mono- or di-lower alkylamino lower hydroxyalkyl; phenyl C$_{1-4}$ alkyl, phenyl C$_{1-4}$ hydroxy-alkyl, diphenyl C$_{1-4}$ alkyl, benzoyl C$_{1-4}$ alkyl, furyl C$_{1-4}$ alkyl, thienyl C$_{1-4}$ alkyl, furoyl C$_{1-4}$ alkyl or thienoyl C$_{1-4}$ alkyl, which groups may be optionally substituted in the aromatic nucleus, and R$^5$ is lower alkyl, whereby the substituents at the 3- and 4-positions of the piperidine ring are in the cis-position. The compounds of the formula may be in the form of their optically active enantiomers and/or their therapeutically acceptable salts. Furthermore the invention provides pharmaceutical compositions possessing cardiovascular activities, in which as active compound at least a compound of the above formula is used. Methods for the preparation of the pharmaceutical compositions and of the active compounds are also disclosed and covered by the invention.

31 Claims, No Drawings

QUINOLINE DERIVATIVES, PHARMACEUTICAL COMPOSITIONS CONTAINING SUCH COMPOUNDS, AND METHODS OF TREATING CARDIOVASCULAR CONDITIONS WITH THEM

The invention relates to novel quinoline derivatives and to pharmaceutical compositions containing these compounds.

French Pat. No. 73,41043 (Publ. No. 2,206,944) discloses quinoline derivatives of the formula:

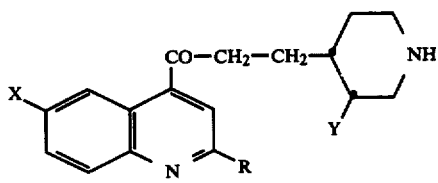

in which X is hydrogen or methoxy, Y is hydrogen, ethyl or vinyl and R is $C_{1-4}$ alkyl, cycloalkyl or optionally substituted aralkyl or aryl, which compounds may be used for the treatment and prophylaxis of cardiovascular affections.

It has now been found, that quinoline derivatives substituted at the 2- and 4-position and optionally at the 6-position, and in which the substituent at the 4-position contains a N-substituted piperidyl group, possess unexpected pharmacological properties, namely desirable effects on the cardiovascular system such as anti-hypertensive, anti-thrombotic, vasodilatory and anti-arrhythmic activity. The compounds are particularly useful for use in medicines administered for the treatment of hypertensive or arrhythmic conditions.

Thus, the invention provides compounds of the formula:

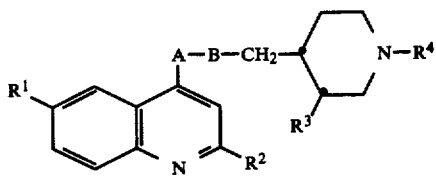

in which
A—B is —$CH_2$—$CH_2$—, —CHOH—$CH_2$—, —$CH_2$—CHOH—, —C(O)—$CH_2$—, —$CH_2$—C(O)—, —C($NOR^5$)—$CH_2$—, or —$CH_2$—C($NOR^5$)—,
$R^1$ is hydrogen, hydroxy or lower alkoxy,
$R^2$ is lower alkyl, hydroxy, lower alkoxy or $CF_3$,
$R^3$ is ethyl or vinyl,
$R^4$ is $C_{1-9}$ alkyl, $C_{2-9}$ hydroxyalkyl or lower alkoxyalkyl, $C_{5-6}$ cycloalkyl, $C_{3-6}$ cycloalkyl lower alkyl, cyano lower alkyl, lower alkenyl, lower alkynyl, tetrahydrofurfuryl, mono- or di-lower alkylamino lower alkyl; mono- or di-lower alkylamino lower hydroxy alkyl; phenyl $C_{1-4}$ alkyl, phenyl $C_{1-4}$ hydroxyalkyl, diphenyl $C_{1-4}$ alkyl, benzoyl $C_{1-4}$ alkyl, furyl $C_{1-4}$ alkyl, thienyl $C_{1-4}$ alkyl, furoyl $C_{1-4}$ alkyl or thienoyl $C_{1-4}$ alkyl, which groups may be optionally substituted in the aromatic nucleus, and
$R^5$ is lower alkyl,
whereby the substituents at the 3- and 4-position of the piperidine ring are in the cis configuration, and acid addition salts thereof.

As is usual, the carbon chains of the different groups may be straight or branched.

The term "lower" is here used to mean a group with up to six carbon atoms.

The term "optionally substituted" with respect to phenyl includes a phenyl group, which may be optionally substituted by one, two or three groups selected from lower alkyl, lower alkoxy, halogen or hydroxy (no more than two hydroxy groups).

The term "optionally substituted" with respect to heteroar(o)yl is used to mean a heteroar(o)yl group, which may be optionally substituted by one, two or three groups selected from lower alkyl, lower alkoxy or halogen.

Suitably, A—B is —$CH_2$—$CH_2$—. Another suitable meaning of A—B is —CHOH—$CH_2$—. Also suitable is the meaning of A—B being —$CH_2$—CHOH—. Suitably, A—B is —C(O)—$CH_2$—. Also suitably, A—B is —$CH_2$—C(O)—. The meaning of A—B being —C(—$NOR^5$)—$CH_2$— is also apt, as well as A—B being —$CH_2$—C($NOR^5$)—$R^5$ being preferably methyl.

Where $R^1$ is alkoxy, it is preferably methoxy. $R^1$ is preferably hydrogen or methoxy. Favourably $R^1$ is hydrogen. favourably $R^1$ is methoxy.

$R^2$ as alkyl is preferably methyl. n-Propyl is also preferred. Other suitable alkyl groups include ethyl, isopropyl, n-butyl, iso-butyl, n-pentyl, iso-pentyl and n-hexyl.

$R^2$ as alkoxy is preferably methoxy. Other suitable alkoxy groups include ethoxy, n-propoxy, iso-propoxy, n-butoxy and n-pentoxy.

Particularly preferred is the meaning of $R^2$ being $CF_3$.

Also suitable is the meaning of $R^2$ being hydroxy.

Suitable values for $R^4$ in the meaning of alkyl include methyl, ethyl, n-propyl, iso-propyl, n-butyl, iso-butyl, n-pentyl, iso-pentyl, n-hexyl, n-heptyl, n-octyl and n-nonyl. Preferably, $R^4$ in this meaning is methyl, ethyl, n-propyl, iso-propyl, n-butyl, iso-butyl or n-pentyl, of which n-propyl, n-butyl and n-pentyl are particularly preferable.

Where $R^4$ is hydroxyalkyl or alkoxyalkyl it is favourably a substituent with the formula —$(CH_2)_n$-C($OR^6$)$R^7R^8$, in which n is 1, 2, 3 or 4, $R^6$ is hydrogen or $C_{1-3}$ alkyl, respectively, $R^7$ is hydrogen or $C_{1-3}$ alkyl and $R^8$ is hydrogen or $C_{1-3}$ alkyl.

Where $R^4$ is cyanoalkyl it is preferably a substituent with the formula —$(CH_2)_n$—CN in which n=3, 4 or 5.

Where $R^4$ is cycloalkylalkyl it is suitably cyclopropylmethyl or cyclobutylmethyl.

Where $R^4$ is alkenyl it is suitably allyl.

$R^4$ as alkynyl is suitably butyn-3-yl.

Suitable values for $R^4$ as mono- or di-alkylaminoalkyl include substituents with the formula —$(CH_2)_n NR^9 R^{10}$, in which n is 2 or 3, $R^9$ is hydrogen or $C_{1-3}$ alkyl and $R^{10}$ is $C_{1-3}$ alkyl.

Suitable values for $R^4$ are optionally substituted phenylalkyl, phenylhydroxyalkyl and diphenylalkyl include benzyl, phenethyl, α-hydroxyphenethyl, benzyl or phenethyl substituted by 1, 2 or 3 methoxy groups and 4,4-di(4-fluorophenyl)butyl.

Suitable values for $R^4$ as optionally substituted benzoylalkyl include benzoylmethyl, 2-benzoylethyl, 3-benzoylpropyl, fluorobenzoylmethyl, 2-(fluorobenzoyl)ethyl, 3-(fluorobenzoyl)propyl, 3-(methoxybenzoyl)propyl, 3-(methylbenzoyl)propyl and 3-(chlorobenzoyl)propyl. Preferably, $R^4$ in this meaning is 3-benzoylpropyl or 3-(4-fluorobenzoyl)propyl.

$R^4$ as optionally substituted fur(o)ylalkyl and thien(o)ylalkyl include 2- and 3-fur(o)ylpropyl and 2- and 3-thien(o)ylpropyl, optionally substituted by a lower alkyl group, preferably methyl.

A particular groups of compounds are those of formula 1, or a salt thereof, in which A—B is —CH$_2$—CH$_2$—, —CHOH—CH$_2$—, —CH$_2$—CHOH—, —C(O)—CH$_2$—, —CH$_2$—C(O)—, —C(NOR$^5$)—CH$_2$— or —CH$_2$—C(NOR$^5$)—, $R^1$ is hydrogen, hydroxy or lower alkoxy, $R^2$ is lower alkyl, hydroxy or lower alkoxy, $R^3$ is ethyl or vinyl, $R^4$ is $C_{1-9}$ alkyl, hydroxyalkyl or lower alkoxyalkyl, $C_{5-6}$ cycloalkyl, $C_{3-6}$ cycloalkyl lower alkyl, cyano lower alkyl, lower alkenyl, lower alkynyl, tetrahydrofurfuryl, mono- or di-lower alkylamino lower alkyl; phenyl $C_{1-4}$ alkyl, phenyl $C_{1-4}$ hydroxyalkyl, diphenyl $C_{1-4}$ alkyl, benzoyl $C_{1-4}$ alkyl, furyl $C_{1-4}$ alkyl, thienyl $C_{1-4}$ alkyl, furoyl $C_{1-4}$ alkyl or thienoyl $C_{1-4}$ alkyl, which groups may be optionally substituted in the aromatic nucleus, and $R^5$ is lower alkyl, whereby the substituents at the 3- and 4-position of the piperidine ring are in the cis configuration.

A particular group of compounds of formula 1 are those of formula 1a,

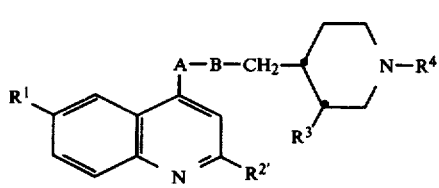

1a in which A—B, $R^1$, $R^3$ and $R^4$ are as defined above and $R^{2'}$ is alkyl. Preferably $R^{2'}$ is methyl or n-propyl. In this group of compounds $R^1$ is preferably hydrogen, $R^3$ preferably ethyl and $R^4$ preferably alkyl or optionally substituted benzoylalkyl, of which n-propyl, n-butyl, n-pentyl, 3-benzoylpropyl and 3-(4-fluorobenzoyl)propyl are most preferred. Particularly preferred are those compounds of formula 1a, in which A—B is —C(O)CH$_2$—, —CHOH—CH$_2$— or —CH$_2$—CH$_2$—.

A group of preferred compounds of formula 1 are those of formula 1b,

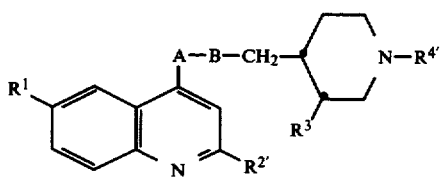

1b in which A—B and $R^3$ are as defined above, $R^{2'}$ is alkyl and $R^{4'}$ is optionally substituted benzoylalkyl. Preferably, $R^{2'}$ is methyl or n-propyl. Preferably, $R^{4'}$ is 3-benzoylpropyl or 3-(4-fluorobenzoyl)propyl, in particular the latter value. Preferably, A—B is —C(O)—CH$_2$—, —CHOH—CH$_2$— or —CH$_2$—CH$_2$—. Preferably, $R^3$ is ethyl.

A group of favourable compounds of formula 1 are those of formula 1c,

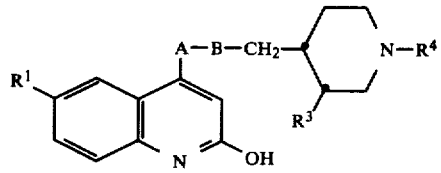

1c in which A—B, $R^1$, $R^3$ and $R^4$ are as previously defined.

Another group of preferred compounds of formula 1 are those of formula 1d,

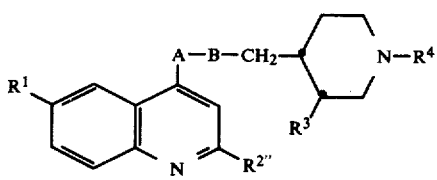

1d in which A—B, $R^1$, $R^3$ and $R^4$ are as defined above and $R^{2''}$ is alkoxy. Preferably, $R^{2''}$ is methoxy or n-propoxy, especially methoxy. Suitable values for A—B include —CH$_2$—CHOH— and —C(O)—CH$_2$—, preferably —CH$_2$—CHOH—. Suitable values for $R^4$ include alkyl, preferably n-propyl, n-butyl, n-pentyl and optionally substituted benzoylalkyl, preferably 3-benzoylpropyl. The preferred value for $R^1$ is hydrogen and for $R^2$ ethyl.

A group of favourable compounds of formula 1 are those of formula 1n,

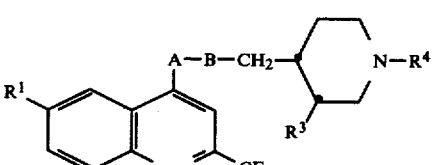

1n in which A—B, $R^1$, $R^3$ and $R^4$ are as previously defined. The preferred values for $R^1$ is hydrogen and methoxy of which hydrogen is most preferred. $R^3$ is preferably ethyl. Suitable values for A—B are —CHOH—CH$_2$—, —CH$_2$—CH$_2$—, —CH$_2$—CHOH— and —CH$_2$—C(O)— of which —CH$_2$—CHOH— is preferred. Suitable values for $R^4$ include alkoxyalkyl preferably 4-methoxybutyl, optionally substituted benzoylalkyl preferably 3-benzoylpropyl and alkyl preferably n-propyl, n-butyl and n-pentyl.

A particular group of compounds of claim 1 are those of formula 1o,

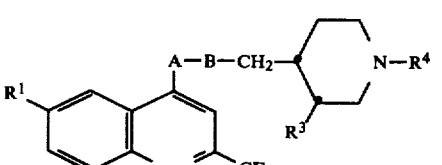

1o in which A—B is —CHOH—CH$_2$— and —CH$_2$—CHOH—, and $R^1$, $R^3$ and $R^4$ are as defined above.

Another particular group of compounds of claim 1 are those of formula 1p,

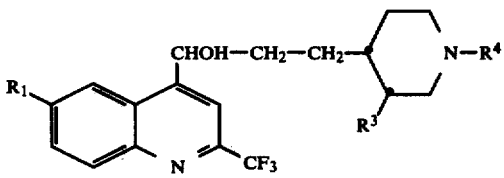

in which $R^4$ is alkyl or alkoxyalkyl and $R^1$ and $R^3$ are as defined above.

A particular group of compounds of claim 1 are furthermore those of formula 1q,

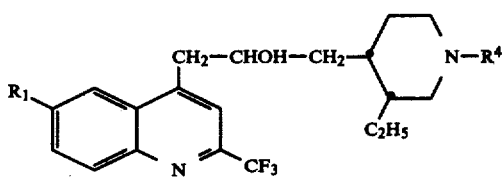

in which $R^1$ is hydrogen or methoxy, and $R^3$ is ethyl and $R^4$ is n-propyl, n-butyl or n-pentyl.

A preferred compound of claim 1 is represented by formula 1r,

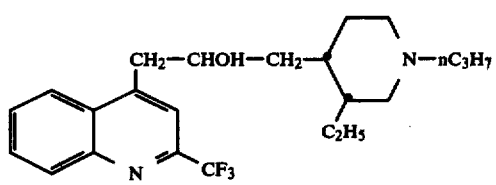

the mixtures of diastereoisomers as well as the separated diastereoisomers.

A further group of suitable compounds of formula 1 are those of formula 1e,

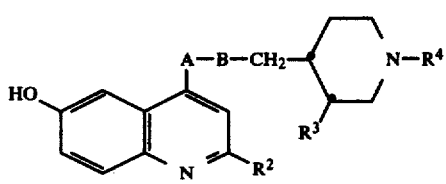

in which A—B, $R^2$, $R^3$ and $R^4$ are as previously defined.

Another group of suitable compounds of formula 1 are those of formula 1f,

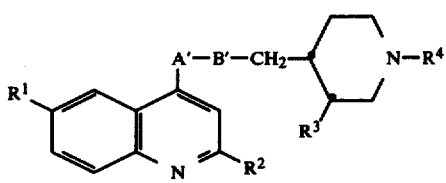

in which A'A—B' is —CHOH—CH$_2$— or —CH$_2$—CHOH— and $R^1$, $R^2$, $R^3$ and $R^4$ are as previously defined. Preferred compounds of this group are especially compounds in which A'—B' is —CHOH—CH$_2$—, $R^1$ is hydrogen, $R^2$ is methyl, $R^3$ is ethyl and $R^4$ is 3-(4-fluorobenzoyl)propyl and in which A'—B' is —CH$_2$—CHOH—, $R^1$ is hydrogen, $R^2$ is methoxy, $R^3$ is ethyl and $R^4$ is n-propyl, respectively.

A further group of suitable compounds of formula 1 are those of formula 1g,

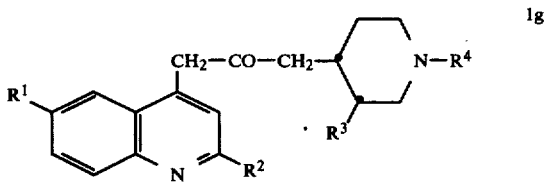

in which $R^1$, $R^2$, $R^3$ and $R^4$ are as defined above, and the O-alkyloxime ethers and especially the O-methyloxime ethers.

Another further group of preferred compounds of formula 1 are those of formula 1h,

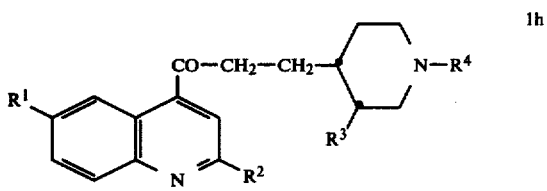

in which $R^1$, $R^2$, $R^3$ and $R^4$ are as defined above, and the O-alkyloxime ethers and especially the O-methyloxime ethers of those compounds. Preferably, $R^1$ is hydrogen, $R^2$ is alkyl, especially methyl or n-propyl, $R^3$ is ethyl and $R^4$ is alkyl or optionally substituted benzoylalkyl, particularly n-propyl, n-butyl or n-pentyl, or 3-benzoylpropyl or 3-(4-fluorobenzoyl)propyl, respectively.

A preferred group of compounds of formula 1 are those in which A—B is —C(O)—CH$_2$—, $R^1$ is hydrogen, $R^2$ is n-propyl, $R^3$ is ethyl and $R^4$ is n-propyl, n-pentyl or 3-benzoyl-n-propyl.

Another group of favourable compounds of formula 1 are those of formula 1i,

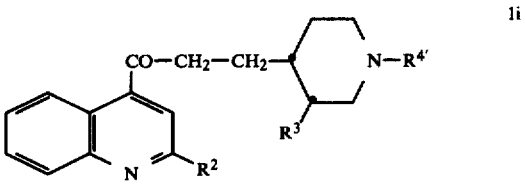

in which $R^2$ and $R^3$ are as defined above, and $R^{4'}$ is optionally substituted benzoylalkyl and preferably 3-(4-fluorobenzoyl)propyl. Preferably $R^2$ is alkyl, especially methyl or n-propyl, or alkoxy, especially methoxy, and $R^3$ is preferably ethyl.

A further group of suitable compounds of formula 1 are those of formula 1j,

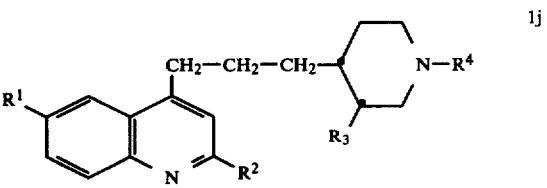

in which $R^1$, $R^2$, $R^3$ and $R^4$ are as previously defined. Preferably in this group $R^1$ is hydrogen, $R^2$ is alkyl, especially methyl, $R^3$ is ethyl and $R^4$ is alkyl or optionally substituted benzoylalkyl, especially n-propyl, n-butyl or n-pentyl and 3-benzoylpropyl, respectively.

Again another group of suitable compounds of formula 1 are those of formula 1k,

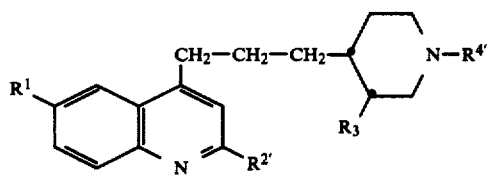

in which $R^1$ and $R^3$ are as defined above, $R^{2'}$ is alkyl and $R^{4'}$ is optionally substituted benzoylalkyl. Preferably in this group $R^1$ is hydrogen, $R^{2'}$ is methyl, $R^3$ is ethyl and $R^{4'}$ is 3-benzoylpropyl.

Another group of compounds of formula 1 are those in which A—B is —CH$_2$—CH$_2$—, $R^1$ is hydrogen, $R^2$ is methyl, $R^3$ is ethyl and $R^4$ is 3-benzoyl-n-propyl or 3-(4-fluorobenzoyl)-n-propyl.

A particular group of compounds of formula 1 are those in which A—B is —CH$_2$—CH$_2$—, $R^1$ is isopentoxy, $R^2$ is methyl, $R^3$ is ethyl and $R^4$ is 3-(4-fluorobenzoyl)-n-propyl.

A further group of favourable compounds of formula 1 are those of formula 1l,

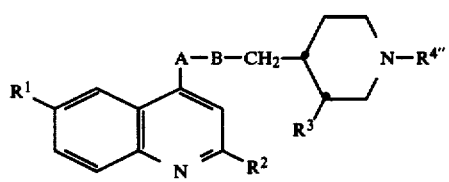

in which A—B, $R^1$, $R^2$ and $R^3$ are as previously defined and $R^{4''}$ is hydroxy alkyl, alkoxyalkyl or cyanoalkyl. If $R^{4''}$ is hydroxyalkyl, the hydroxy group is attached to the β- carbon atom such as for example 2-hydroxy-2-methylpropyl. If $R^{4''}$ is alkoxyalkyl the values 3-methoxypropyl, 4-methoxybutyl or 5-methoxypentyl are preferred, whereas if $R^{4''}$ is cyanoalkyl the values 4-cyanobutyl and 5-cyanopentyl are favourable.

Another group of favourable compounds of formula 1 are those of formula 1m,

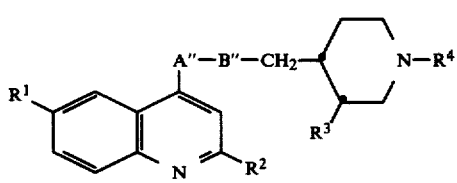

in which A''—B'' is —C(NOR$^5$)—CH$_2$—, or —CH$_2$—C(NOR$^5$)— and $R^1$, $R^2$, $R^3$, $R^4$ and $R^5$ are as defined above.

Preferably $R^5$ is methyl.

A further group of compounds of formula 1 are those in which A—B is —C(NOR$^5$)—CH$_2$—, $R^1$ is hydrogen, $R^2$ is methyl, $R^3$ is ethyl and $R^4$ is (2-hydroxy-2-methyl)-n-propyl.

A particular group of compounds of formula 1 are those in which A—B is —CHOH—CH$_2$—, $R^1$ is hydrogen, $R^2$ is methyl, $R^3$ is ethyl and $R^4$ is 3-(4-fluorobenzoyl)-n-propyl.

Another group of compounds of formula 1 are those in which A—B is —CHOH—CH$_2$—, $R^2$ is methyl, $R^3$ is ethyl, $R^4$ is n-propyl and $R^1$ is hydrogen or methoxy.

A further group of compounds of formula 1 are those in which A—B is —CO—CH$_2$, $R^1$ is hydrogen, $R^2$ is isopropyl, $R^3$ is ethyl and $R^4$ is (2-hydroxy-2-methyl)-n-propyl.

A suitable group of compounds of formula 1 are those in which A—B is —CH$_2$—CHOH—, $R^1$ is hydrogen, $R^2$ is methoxy, $R^3$ is ethyl and $R^4$ is n-propyl or 3-benzoyl-n-propyl.

From the foregoing it will be appreciated that the following compounds according to the invention are particularly preferred.

N-propyl-2'-trifluoromethyl-hydrocinchonicinol-2, isomer I thereof, isomer II thereof, mixture of isomers;
N-propyl-2'-methyl-hydrocinchonicine;
N-propyl-2'-propyl-hydrocinchonicine;
N-pentyl-2'-propyl-hydrocinchonicine;
N-(3-benzoylpropyl)-2'-propyl-hydrocinchonicine;
N-propyl-2'-propyl-hydrocinchonicinol-1;
N-propyl-2'-propyl-hydroquinicinol-1;
N-(3-benzoylpropyl-2'-propyl-hydrocinchonicinol-1;
N-propyl-2'-methyl-hydrocinchonicinol-1;
N-propyl-2'-methyl-hydroquinicinol-1;
N-[3-(4-fluorobenzoyl)propyl]-2'-methyl-hydrocinchonicinol-1;
N-(2-hydroxy-2-methylpropyl)-2'-methyl-hydrocinchonicine-O-methyl oxime ether;
N-(2-hydroxy-2-methylpropyl)-2'-isopropyl-hydrocinchonicine;
N-pentyl-2'-methyl-desoxo-hydrocinchonicine;
N-(3-benzoylpropyl)-2'-methyl-desoxo-hydrocinchonicine;
N-[3-(4-fluorobenzoyl)propyl]-2'-methyl-desoxo-hydrocinchonicine;
N-[3-(4-fluorobenzoyl)propyl]-2'methyl-6'-isopentoxyoxy-desoxo-hydrocinchonicine;
N-propyl-2'-methoxy-hydrocinchonicinol-2;
N-(3-benzoylpropyl)-2'-methoxy-hydrocinchonicinol-2.

The preceding compounds of formula 1 may exist in free base form or in the form of their acid addition salts, for example their salts with mineral acids, e.g. hydrochloric acid, hydrobromic acid or sulphuric acid, or with organic acids e.g. acetic acid, fumaric acid or tartaric acid. Naturally the acid used will be pharmaceutically acceptable when such salts are intended for internal administration.

The compounds of formula 1 in which A or B is —CHOH— contain an asymmetric carbon atom and therefore two stereoisomers may exist, provided that there are no assymetric carbon atoms in a side chain. One or more asymmetric carbon atoms in the N-substituent may give rise to several diastereoisomeric forms.

The compounds of the invention may be obtainable in crystalline form. They may also be obtained in the form of solvates such as hydrates.

The compounds of the invention, as represented by formula 1, include free base and acid addition salt forms, mixtures of diastereoisomers and separated forms thereof as well as the quaternary salts.

The invention also provides a process for the preparation of compounds of formula 1, in which (A) a compound of formula 3,

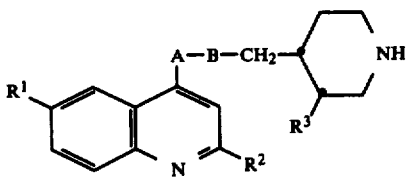

in which A—B, $R^1$, $R^2$ and $R^3$ are as defined above, is alkylated with a compound $R^4Y$, in which $R^4$ is as defined above and Y is a nucleophilic leaving group, particularly chlorine, bromine, iodine, aryl-, aralkyl- or alkylsulphonyloxy and especially mesyloxy or tosyloxy, or (B) a compound of formula 4,

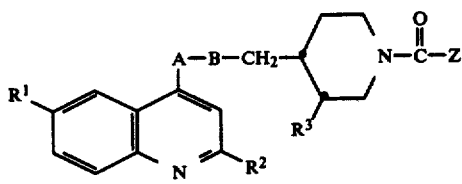

in which A—B, $R^1$, $R^2$ and $R^3$ are as defined above, is reduced, to give a compound in which $R^4$ contains an α-methylene group, or (C) a compound of formula 3 above is reacted with an epoxide of formula 5,

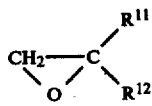

in which $R^{11}$ is $C_{1-7}$ alkyl, optionally substituted phenyl or optionally substituted phenyl $C_{1-2}$ alkyl, and $R^{12}$ is hydrogen or lower alkyl, to give a compound of formula 1, in which $R^4$ is

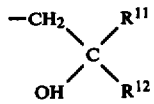

as defined above, or (D) a compound of formula 1, in which $R^4$ contains a hydroxy group, is alkylated, or (E) a compound with formula 3 above is reacted with a compound of formula 14

in which p' and q' are defined by that p'q'CH— will be identical with $R^4$, in the presence of a reducing agent, or (F) a compound of formula 1 in which A—B is —CH$_2$—CO— or —CH$_2$—CHOH— and $R^2$ is alkoxy or trifluoromethyl is prepared by reacting a compound of formula 15

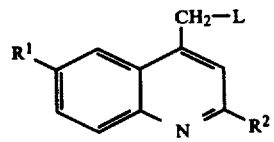

in which $R^1$ is hydrogen or alkoxy and $R^2$ is alkoxy or $CF_3$ and L is an alkali atom preferable a lithium atom, with a piperidine derivative of formula 16

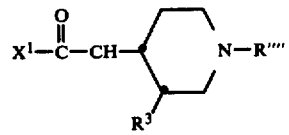

in which $X^1$ is alkoxy or hydrogen respectively and $R^3$ is as defined for formula 1 and $R^{4''''}$ is an inert group selected from the meaning of $R^4$ of formula 1.

In method A, the reaction is preferably carried out by using an equivalent amount or a small excess of the alkylation agent $R^4Y$. Suitably an acid binding agent is used which does not react with the alkylating agent. For this purpose sterically hindered amines, e.g. dicyclohexylethylamine can be used, but generally inorganic bases such as sodium or potassium carbonate and especially sodium or potassium bicarbonate are preferred. It may also be advantageous to accelerate the reaction by adding a catalytic or equivalent amount of an iodide.

The reaction is preferably carried out in an inert organic solvent e.g. acetone, butanone, methyl ethyl ketone, methyl isobutyl ketone, tetrahydrofuran, dimethylformamide, dimethylsulphoxide, dioxane, methylene chloride, chloroform, benzene, toluene, xylene or a mixture of such solvents. Methyl ethyl ketone, dimethylformamide and toluene or mixtures thereof are preferred. Generally the reaction may be run from 0° C. to the boiling point of the solvent.

In method B the reduction is preferably carried out using diborane or a complex hydride, such as lithium aluminium hydride. The hydride is added in equivalent amounts or in excess, preferably in quantities up to triple the equivalent amounts. The reduction is preferably carried out in an inert solvent, in particular tetrahydrofuran, at a reaction temperature between 0° C. and the boiling point of the solvent.

It must be noted that such reducing agent will also be able to reduce carbonyl to alcohol groups. In compounds of formula 4 in which A or B is —(CO)—, these groups usually will be converted into compounds of formula 1 in which A or B is reduced to —CHOH—. In particular cases in which A or B is —C(O)—, this reduction may lead to the corresponding compounds with A or B is —CH$_2$—.

The compounds of formula 4 may be prepared for example by acylation of a compound of formula 3 with a compound of formula 6,

in which X is halogen or —OCOZ and Z is $R^4$ minus a terminal methylene group.

The acylation of the compound of formula 3 is preferably carried out in the presence of an acid binding agent, particularly triethylamine or pyridine. Suitable solvents include chloroform, pyridine or dimethyl formamide. Usually the reaction temperature is between 0° C. and the boiling point of the reaction mixture.

The compounds of formula 4 may also be prepared by reaction of a compound of formula 3 with a carboxylic acid of formula 7,

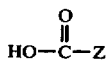

$$HO-\underset{\underset{O}{\|}}{C}-Z \qquad 7$$

in which Z is as defined above, in the presence of dicyclohexylcarbodiimide. This acylation method is effected under normal conditions, e.g. in chloroform as a solvent, after which the reaction product is isolated in conventional manner.

Method B is advantageous for the preparation of compounds of formula 1 in which $R^4$ contains a branched alkoxyalkyl group.

Method C is suitably carried out in an inert organic solvent, preferably a lower alcohol of 1-5 carbon atoms or in a mixture of such an alcohol with dichloromethane. Sometimes it is advantageous to add water to the reaction mixture.

The reaction conditions usually depend on the reactivity of the epoxide. Usually the reaction may be run for some hours and is preferably effected at temperatures between 20° and 120° C. Where a volatile epoxide is used, a closed system may be necessary.

In method D, the hydroxy group is suitably first converted into the corresponding alkali salt, e.g. with sodium hydride in an aprotic solvent. This salt is then treated with an alkyl halide or an alkyl or aryl sulphonic ester, preferably with an alkyl halide.

Method E is suitably carried out with hydrogen as reducing agent in the presence of a catalyst, for example palladium on coal. Depending on the catalyst of choice hydrogen pressures of 1-150 at are involved. The reaction conditions are as commonly used for this type of reaction. The reaction is suitably carried out in a solvent, such as a lower alcohol, preferably methanol or ethanol at a temperature generally in the range of 20°-100° C., preferably between 20°-40° C.

Another suitable method in which the use of high pressure is avoided comprises the reaction of the compounds of formulae 3 and 14 in the presence of an equivalent amount of sodium cyanoborohydride and a base, such as potassium hydroxide. The reaction is suitably carried out at room temperature, in a solvent such as an alcohol, preferably methanol or ethanol.

Method F is particularly suitable to prepare compounds of formula 1 with A-B is —CH₂—C(O)— or —CH₂—CHOH— and $R^2$ is alkoxy or trifluoromethyl. This method is based on a method described in J. Am. Chem. Soc. 100, 576–581 (1978) and uses the condensation of a 4-methylquinoline which is substituted at the 2-position with an alkoxy or trifluoromethyl group and optionally substituted at the 6-position, with an ester of a 4-piperidylacetic acid derivative of formula 16, already containing a suitable substituent $R^{4''''}$ under the influence of lithium and a strong base.

Suitable solvents-systems include mixtures of tetrahydrofuran, benzene and diethylether. Preferred temperatures are between −80° C. and 0° C.

It will be clear that the substituent $R^{4''''}$ may not contain groups which are reactive under the conditions to be used. Alternatively, such groups have to be protected.

The starting compounds of formula 3 are new for the greater part. In most cases, however, they amy be prepared in a manner known for the synthesis of analogous compounds.

In the above-cited French Pat. No. 73,41043 the preparation according to two different methods is described of compounds of formula 2, in which X is hydrogen or methoxy, Y is among other things ethyl and vinyl and R is among other things $C_{1-4}$ alkyl. The starting material in the first method is a suitable cinchona alkaloid, such as quinine, cinchonine or the hydroderivatives of these compounds, which is converted into the corresponding ar-mono-N-oxide in a manner known per se, which compound is then converted with a lithium or Grignard compound into a cinchona alkaloid substituted at the 2'-position by alkyl (or cycloalkyl, aralkyl or aryl).

The resulting compounds are converted in conventional manner into the so-called open compounds of formula 2 by reacting with moderately diluted acid at elevated temperature.

The second method described in said French patent is based on the condensation of an ester of 3-(4-piperidyl)-propionic acid with a quinoline derivative, which is substituted at the 4-position by a carboxylic ester group or a lithium atom.

J. Amer. Chem. Soc. 100, 576–581 (1978) discloses the preparation of a compound of formula 8,

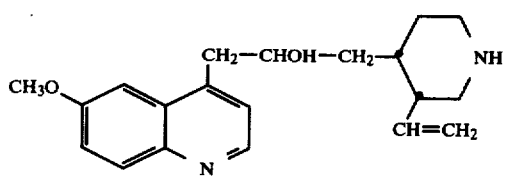

by converting 6-methoxylepidine in situ to 6-methoxylepidyllithium and reacting this compound with the methyl ester of a 4-piperidyl acetic acid derivative (e.g. N-benzoylmeroquinene methyl ester). While removing the N-benzoyl group of the resulting keto compound of the 1,3-disubstituted propanone-2 type, the compound is reduced to a propanol-2 derivative.

The starting compounds of formula 3 which may be used for the preparation of the new compounds of formula 1 according to the invention, in which $R^2$ is an alkyl group and A-B is a —C(O)—CH₂— group, may be advantageously prepared in a way analogous to the French Patent, starting from compounds of formula 9,

in which $R^1$ and $R^3$ are as defined before.

The hydramine splitting of the cinchona alkaloid, which is substituted at the 2'-position by alkyl, to a compound of formula 3 defined above, is preferably carried out with moderately diluted acetic acid or sulphuric acid, preferably at a temperature of about 100° C. to the boiling point of the mixture.

The required 2'-unsubstituted ar-mono-N-oxide compounds of formula 10,

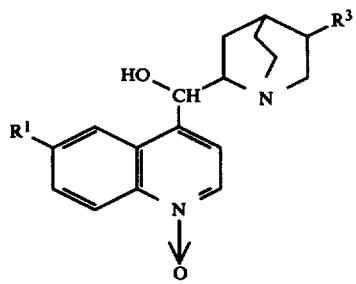

in which $R^1$ and $R^3$ are as defined above, are known or may be obtained in an analogous way from known compounds. The starting 2'-unsubstituted cinchona alkaloid is preferably unsubstituted at the 6'-position or substituted by a methoxy group.

The compounds of formula 3 thus obtained, in which $R^2$ is alkyl and A-B is —C(O)—$CH_2$— may be converted in conventional manner by complete or partial reduction to the corresponding —$CH_2$—$CH_2$— or —CHOH—$CH_2$— compounds, respectively. A suitable reducing agent for the conversion to the desoxo compound (—$CH_2$—$CH_2$—) is e.g. hydrazine hydrate, in the presence of an alkali metal hydroxide, such as potassium hydroxide, in a suitable solvent such as an alcohol, e.g. ethylene glycol. A suitable reducing agent for the partial reduction to the alcohol derivative (—CHOH—$CH_2$—) is for example a complex hydride, such as sodium borohydride. This reduction is advantageously carried out at a temperature of about −5° to −10° C. in a suitable solvent, like an alcohol, e.g. isopropylalcohol. If desired, the alcohol compound may also be converted into the corresponding desoxo compound, e.g. by converting the alcohol in a suitable solvent, such as tetrachloromethane ($CCl_4$), with phosphorus pentachloride to the chloride and reducing the resulting compound, for example with hydrogen gas in a solvent, such as ethylalcohol and for example palladium on coal as a catalyst.

Compounds of formula 3 in which $R^2$ is alkyl and A-B is —$CH_2$—CHOH—, may be prepared e.g. by reduction of a cis- or trans-oxirane compound of formula 11,

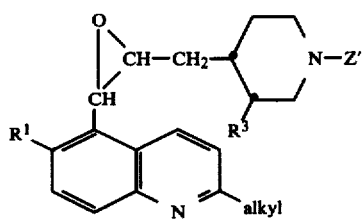

in which $R^1$ and $R^3$ are as defined above and Z' is a protecting group and preferably benzyl, followed by removal of this protecting group in conventional manner. The reduction is suitably carried out by leading hydrogen gas through a suitable solvent, such as an alcohol, e.g. ethylalcohol, in the presence of a suitable catalyst, e.g. palladium on coal, at room temperature or slightly elevated temperature. As a result of the reduction generally alcohols are formed as a mixture of diastereoisomers, which may be separated in conventional manner. The removal of the protecting group may be carried out with known techniques. If the protecting group is alkyl, this group may be removed e.g. with cyanogen bromide or chlorocarbonic acid ester. If the protecting group is a benzyl group, debenzylation occurs preferably catalytically.

It is noted, that the protecting group Z' may have the meaning of $R^4$, which is previously defined. In that case the reduction will result into a compound with formula 1, so that the removal of the protecting group may be omitted.

The preparation of the cis- and trans-oxirane compounds of formula 11 has been described by L. Keefer, Thesis Univ. of New Hampshire 1966 and G. G. Lyle and L. K. Keefer, Tetrahedron 23, 3253–3263 (1967) or may be prepared in an analogous way. Generally, the compounds may suitably be prepared by quaternizing a compound of formula 9 in conventional manner, for example to the corresponding benzobromide and converting the resulting compound with a base.

Because of the stereospecificy of the reaction a compound of formula 9 in the erythro configuration is preferably used as the starting material, while the quaternizing group is not too small, i.e. larger than methyl and ethyl. Thus, a suitable group is for example benzyl. The reaction with the quaternizing compound is suitably carried out with a base, such as potassium hydroxide in a solvent, such as ethylalcohol.

It is noted, that if the above-described reaction is carried out with the quaternizing salt of a threo compound of formula 9, a keto compound of formula 12

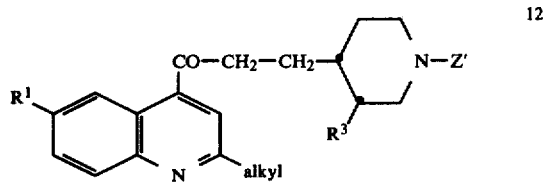

may be formed, in which $R^1$, $R^3$ and Z' are as previously defined. If a relatively small quaternizing group is used, such as a methyl group, generally a keto compound of formula 12 is formed in this reaction, both if a threo or an erythro compound of formula 9 is the starting material. Therefore, this method is also suitable for the preparation of compounds of formula 1, in which A-B is —C(O)—$CH_2$— and, after removal of the protecting group Z', of the corresponding compounds of formula 3.

Threo compounds of formula 9 may also be converted to oxirane compounds of formula 11, if the quaternizing group is not too small, e.g. benzyl. This reaction is carried out with a strong base, in which B⁻ is bulky, for example potassium t-butoxide in t-butanol. The resulting oxirane compound is usually in the cis-configuration.

The resulting compounds of formula 3, in which $R^1$ and $R^3$ are as previously defined and $R^2$ is alkyl and A-B is —$CH_2$—CHOH—, may be oxidized in conventional manner to the corresponding keto compounds, in which A-B is —$CH_2$—C(O)—. A suitable method includes the Oppenauer oxidation. Such keto compounds may also be prepared by the cited second method from French Patent 73,41043 or the method described in J. A. Chem. Soc. 100, 576-581 (1978), for example by condensing 4-methylquinoline which is substituted at the 2-position and optionally substituted at the 6-position, with the ester of a 4-piperidylacetic acid derivative under the influence of lithium and a strong base.

The starting compounds of formula 3, in which $R^2$ is alkoxy, may be obtained by quaternizing a compound of formula 13,

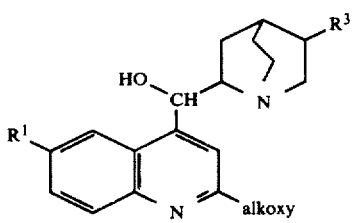

in which $R^1$ and $R^3$ have the previously defined meanings, and converting this compound with a base. In the same way as described above in relation to the corresponding 2'-alkyl compounds, compounds may be obtained according to this method, in which A-B is —C(O)—CH$_2$— or —CH$_2$—CHOH—, depending particularly on the isomer used as the starting compound, the size of the quaternizing group and the base used.

The resulting —C(O)—CH$_2$— or —CH$_2$—CHOH— compounds may be further converted to the corresponding —CHOH—CH$_2$—, —CH$_2$—CH$_2$— or —CH$_2$—C(O)— compounds in a way already described. It is noted that the 2'-alkoxy group is easily converted to a 2'-hydroxy under the influence of diluted acid. For the preparation of 2'-hydroxy compounds of formula 1 or 3 the corresponding 2'-alkoxy compound is therefore the preferred starting compound. It will also be appreciated that 2'-hydroxy compounds may be easily converted to 2'-alkoxy compounds, for example by converting the hydroxy group to an alkali salt with a solution of alkali hydroxide and treating this compound with an dialkyl sulphate.

Compounds with formula 1, in which $R^2$ is hydroxy, may be also prepared starting from the corresponding 2'-unsubstituted compounds, e.g. by converting these compounds with m-chloroperbenzoic acid to the ar-mono-N-oxide, converting the resulting compound for example with phosphoroxytrichloride to the 2'-chloro compound and hydrolyzing this compound. It is noted that, if is started with a 2'-unsubstituted compound in which A or B is a carbonyl group, this group must be protected, for example by converting it to a ketale or thioketale according to conventional methods. It will be appreciated to those skilled in the art that in the same way also a 2'-alkoxy and, if desired, a 2'-alkyl group may be introduced in compounds of formula 1 or 3, which are unsubstituted at the 2'-position.

The starting compounds of formula 13 are either known or may be obtained in analogous manner from known compounds. A suitable method for preparing these starting compounds is for example the conversion of a compound of formula 10 with phosphoroxytrichloride to a cinchona alkaloid which is substituted at the 2'-position by chlorine, which compound may be converted with a suitable alkoxide to the corresponding 2'-alkoxy compound. Hydrolysis of the 2'-chloro compound affords directly the 2'-hydroxy compound.

The starting compound of formula 3, in which A-B is —C(NOR$^5$)—CH$_2$— or —CH$_2$—C(NOR$^5$)—, may be obtained for example by reacting the corresponding carbonyl compound with an O-substituted hydroxylamine derivative of formula $R^5$O—NH$_2$, in which $R^5$ is as previously defined. This reaction is carried out in conventional manner for this type of reaction. Preferably, the reaction is carried out in a solvent, such as an alcohol, dioxane, dimethyl formamide or pyridine, at a temperature generally between room temperature and the boiling point of the reaction mixture. The hydroxylamine derivative is usually added as an acid salt, preferably the hydrochloride, which salt is preferably dissolved in pyridine.

It will be appreciated by those skilled in the art, that the conversion of the carbonyl group to the oxime ether group may occur with both the carbonyl compounds of formula 1 and formula 3.

Compounds of formula 1 or 3 possessing an alkoxy group at the 6'-position and wherein $R^3$ is vinyl, are preferably converted to the corresponding 6'-hydroxy compounds with boron tribromide, which compounds may be converted in the same or another 6'-alkoxy compound in conventional manner, preferably with the aid of a mesyl ester. The 6'-alkoxy compounds in which $R^3$ is ethyl may be also converted to 6'-hydroxy compounds with 48% hydrobromic acid.

The reaction products from any method A-F may be isolated from the reaction mixture and purified by conventional means.

In a number of cases, certain reaction steps may be carried out in a different sequence or simultaneously or without isolating intermediates, and these possibilities are all included in the invention.

Those skilled in the art will appreciate that protecting groups may be used to protect certain reactive functions during the above processes, in accordance with conventional chemical practice.

Certain compounds of formula 1 may also be used for the preparation of other compounds of formula 1 and are therefore also suitable as intermediates.

Diastereoisomers may be separated by known techniques, based on their different physical and chemical characteristics e.g. by fractional crystallization or by column chromatography. These isomer separations may be effected after the final step of the synthesis used or optionally at a previous step, after the formation of the mixture of diastereoisomers.

The free base and acid addition salt forms of the compounds of formula 1 may be interconverted by standard methods.

The compounds of formula 1 possess pharmacological activity. In particular they possess cardiovascular activity, for example anti-hypertensive, anti-thrombotic, vasoliIatory and anti-arrhythmic activity.

An indicated suitable daily dosage (for a 70 kg human) is from 1 to 200 mg, of a compound of formula 1, preferably administered in divided dosages of from 0.5 mg to 50 mg 2 to 4 times daily, or in retard form. Orally administrable unit dose forms may thus contain 0.5, 1, 2.5, 5, 10, 20, 25 or 50 mg of an active ingredient.

The compounds may be administered in free base form or in the form of their pharmaceutically acceptable acid addition salt forms, which salt forms have the same order of activity as the free base forms.

The compounds of formula 1 may be admixed with conventional pharmaceutically acceptable diluents or carriers and, optionally, other excipients, and administered for example in such forms as tablets, capsules and injectable solutions. They may be administered in combination preparations with other active agents.

The pharmaceutical compositions may be formulated in conventional manner, e.g. as for other anti-hypertensive agents.

The following Examples illustrate the invention.

EXAMPLE 1

2'-Methyl-hydrocinchonicine.bifumarate (intermediate)

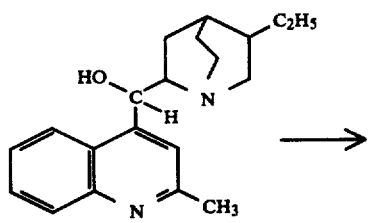

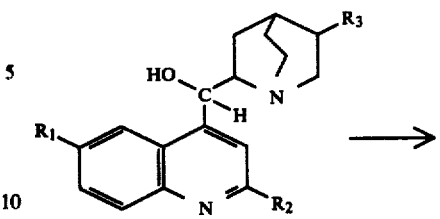

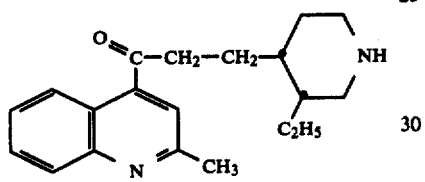

| Example | R$_1$ | R$_2$ | R$_3$ | m.p.°C./salt | |
|---|---|---|---|---|---|
| 2 | H | CH$_3$ | CH=CH$_2$ | 166-168 | BF |
| 3 | OCH$_3$ | CH$_3$ | CH$_2$—CH$_3$ | oil | |
| 4 | H | (CH$_2$)$_2$—CH$_3$ | CH$_2$—CH$_3$ | 148-152 | TO |
| 5 | H | CH(CH$_3$)$_2$ | CH$_2$—CH$_3$ | 97 | BO |

BF = bifumarate (mol. ratio 1:1)
TO = tetraoxalate (mol. ratio 1:2)
BO = bioxalate (mol. ratio 1:1)

2'-Methyl-hydrocinchonidine, 167 g (538 mmol), was dissolved in 180 g (3 mol) of glacial acetic acid, after which 1500 ml of water were added. The mixture was refluxed for 48 h and the conversion was followed by thin layer chromatography. After it was found that the reaction was substantially completed, the reaction mixture was poured on 500 g of ice, to which 100 g of sodium hydroxide were added. The mixture was then extracted three times with 250 ml of toluene, the layers were separated and the collected toluene fractions were dried over magnesium sulphate. The solution was filtered and concentrated in vacuo to a volume of about 250 ml. The solution was filtered over a short silica gel column with chloroform as the eluent. The fractions with the desired product were evaporated in vacuo, after which the resulting residue (145.6 g) was dissolved in 2500 ml of acetone, and 54.3 g (468 mmol) of fumaric acid were added. After heating and cooling the mixture the 2'-methyl-hydrocinchonicine was obtained as the bifumarate. Melting point 159°-160° C.

The base required for further conversion was obtained by dissolving the bifumarate in water, making the solution alkaline with 4 N sodium hydroxide (pH 9-10) and extracting it with toluene. After separating the layers the toluene layer was dried with molecular sieves, filtered and evaporated to dryness in vacuo. The base remained as an oil.

In the same way the following compounds (intermediates) were prepared:

EXAMPLE 6

6'-Isopentoxy-2'-methyl-hydrocinchonicine.bioxalate (intermediate)

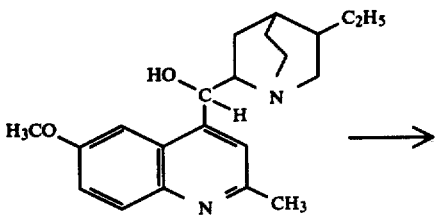

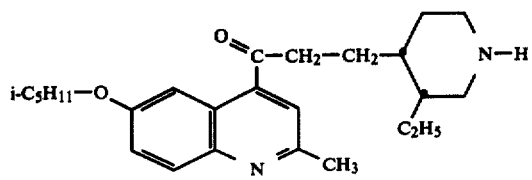

2'-Methyl-hydroquinine (21 g) was refluxed with 200 ml of 47% hydrobromic acid for 17 hours. After cooling and neutralizing with concentrated ammonia to pH 7-8, the 2'-methyl-6'-hydroxy-hydrocinchonidine formed was extracted three times with 100 ml of chloroform. The chloroform fraction was evaporated in vacuo to dryness, after which the residue was dissolved in methyl ethyl ketone. An equivalent amount of hydrochloric acid, dissolved in isopropylalcohol was then added. After crystallization and recrystallization the 2'-methyl-6'-hydroxyhydrocinchonidine.hydrochloride was obtained, melting point 220°-222° C.

The product so obtained was suspended in 180 ml of n-pentanol, to which 8 g of potassium hydroxide were added. After stirring for 10 minutes 10.6 g methane sulphonic acid isopentylester were added under nitrogen. The mixture was then heated at 40° C. for 30 hours while stirring. After the conversion was found to be substantially completed with the aid of thin layer chromatography, 90 ml of 2 N hydrochloric acid were added. The solvent was removed by steam distillation, after which sufficient 2 N sodium hydroxide was added to pH 12 and the resulting product was extracted three times with 100 ml of chloroform. The chloroform fraction was evaporated in vacuo to dryness, after which the crude 2'-methyl-6'-isopentoxy-hydrocinchonidine was obtained as an oil.

In the same way as described in Example 1 the obtained product was converted to 2'-methyl-6'-isopentoxy-hydrocinchonicine. Melting point of the bioxalate 154°–155° C.

EXAMPLE 7

2'-Propyl-hydrocinchonicinol-1 (intermediate)

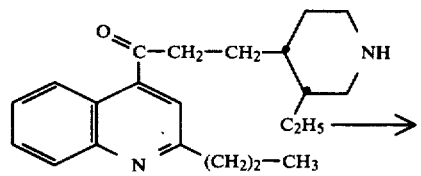

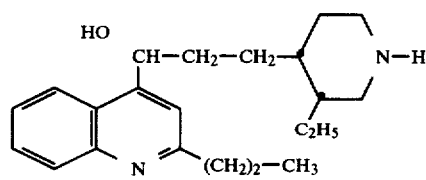

2'-Propyl-hydrocinchonicine (Example 4), 50 g (150 mmol) was dissolved in 225 ml of isopropylalchol, after which the mixture was cooled to −10° C. A solution of 11.5 g (300 mmol) of sodium borohydride in 225 ml of isopropylalcohol was then added in such a way that the temperature dit not exceed −5° C. The mixture was stirred for another 1 hour at −10° C. till the conversion was substantially completed. The conversion was followed with thin layer chromatography. The mixture was then allowed to rise to room temperature, after which 250 ml of water was added. The mixture was extracted three times with 250 ml of chloroform. The collected chloroform fractions were evaporated at reduced pressure, which afforded the title compound as an oil.

In the same way the following compounds (intermediates) were prepared:

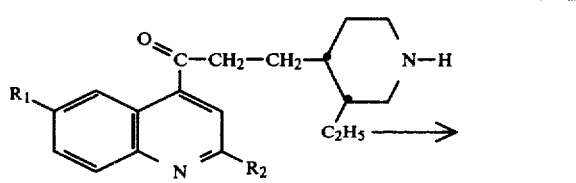

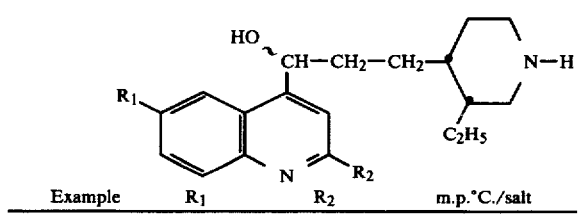

| Example | $R_1$ | $R_2$ | m.p.°C./salt |
|---|---|---|---|
| 8 | H | $CH_3$ | oil |
| 9 | $OCH_3$ | $CH_3$ | oil |
| 10 | $OCH_3$ | $(CH_2)_2-CH_3$ | oil |
| 11 | H | $(CH_2)_2-CH_3$ | 132   TO |

TO = tetra-oxalate (mol. ratio 1:2)

EXAMPLE 12

2'-Methyl-desoxo-hydrocinchonicine.dihydrochloride (intermediate)

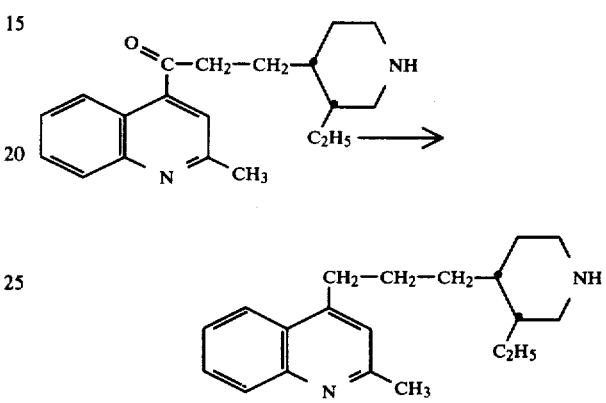

2'-Methyl-hydrocinchonicine (Example 1), 71 g (229 mmol), was dissolved in 200 ml of ethylene glycol, after which 20 ml of 80% hydrazine hydrate were added. The mixture was heated till 140°–145° C. in a nitrogen atmosphere and water was removed during 2 hours with a Dean-Stark apparatus. Then 30 g of potassium hydroxide were added to the reaction mixture in about 30 minutes, which caused evolution of nitrogen. After the addition of potassium hydroxide was completed the mixture was heated at 140° C. for another 2 hours. After cooling 250 ml of water were added, after which the mixture was extracted twice with 250 ml of toluene. The collected toluene fractions were washed twice with 250 ml of water and dried over molecular sieves. After filtration and evaporation at reduced pressure the crude reaction product was obtained, which was dissolved in 200 ml of methyl ethyl ketone. With the aid of an equivalent amount of hydrochloric acid, dissolved in isopropylalcohol, the 2'-methyl-desoxohydrocinchonicine was obtained from this solution after heating and cooling, as its dihydrochloride. Melting point after recrystallization form methyl ethyl ketone: 192°–196° C.

EXAMPLE 13

6'-Isopentoxy-2'-methyl-desoxo-hydrocinchonicine (intermediate)

In the same way as described in Example 12 6'-isopentoxy-2'-methyl-hydrocinchonicine (Example 6) was converted into 6'-isopentoxy-2'-methyl-desoxohydrocinchonicine. The compound was obtained as an oil.

EXAMPLE 14

2'-Methoxy-hydrocinchonicinol-2.dihydrate
(intermediate)

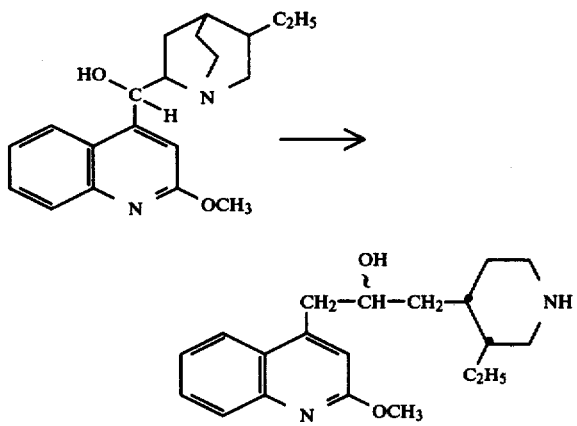

2'-Methoxy-hydrocinchonidine, 9.8 g (30 mmol), which was obtained in the same way as the corresponding known 2',6'-dimethoxy-hydrocinchonidine, was dissolved in 50 ml of absolute ethylalcohol, after which 5.6 g (33 mmol) of benzyl bromide were added. The mixture was refluxed for 6 hours, after which the conversion into the quaternary salt was found complete. The reaction mixture was poured into water and extracted twice with 100 ml of chloroform. After drying and evaporation in vacuo the quaternary salt was obtained, which was then dissolved in 50 ml of 96% ethylalcohol. To this solution 100 ml of 10% potassium hydroxide were added. The mixture was refluxed for 1 hour giving rise to the N-benzyl-2'-methoxy-hydrocinchonicine-1,2-epoxide. The mixture was poured into water, after which the resulting oxirane was extracted twice with 100 ml of ethyl acetate. The collected fractions were dried over magnesium sulphate, filtered and evaporated to dryness in vacuo, affording the oxirane as an oil.

The resulting oil was dissolved in 75 ml of absolute ethylalcohol, to which 2 g of palladium (5%) on active coal were added. Then hydrogen gas was led through the solution. After 650 ml of hydrogen were taken up in the first instance at room temperature and at atmospheric pressure, another 550 ml of hydrogen were taken up after heating to 60° C. The reaction product was filtered and evaporated in vacuo to dryness. The resulting crude product was dissolved in chloroform and purified with column chromatography (silica gel/toluene-methanol 10:1). After evaporation in vacuo, crystallization and recrystallization form cyclohexane the 2'-methoxy-hydrocinchonicinol-2 was obtaeind as its dihydrate. Melting point 198°–199° C.

EXAMPLE 15

2'-Methoxy-hydroquinicinol-2 (intermediate)

In the same way as described in Example 14 but starting with 2'-methoxy-hydroquinone in stead of 2'-methoxyhydrocinchonidine the title compound was obtaind as an oil.

EXAMPLE 16

2'-Hydroxy-desoxo-hydrocinchonicine.bioxalate
(intermediate)

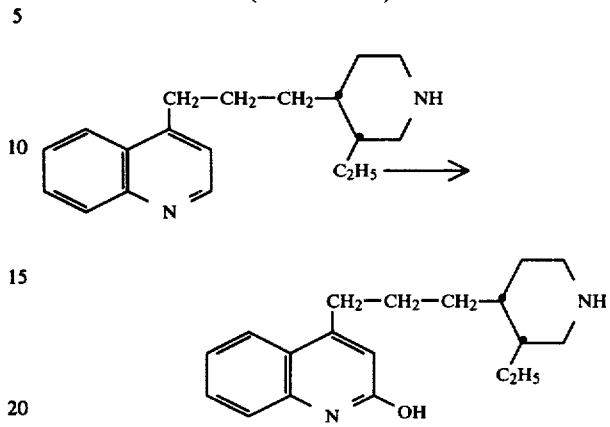

Desoxo-hydrocinchonicine.bioxalate (20 g) with a melting point of 156°–158° C. was suspended at room temperature in 100 ml of absolute ethylalcohol. To this suspension 32.7 g m-chloroperbenzoic acid, dissolved in 50 ml of absolute ethylalcohol were added dropwise in 1 hour in such a way that the temperature of the reaction mixture did not exceed 45° C. After it was found by thin layer chromatography that the conversion of the starting material was substantially complete, $SO_2$ gas was introduced uner cooling until no more peroxide could be traced. The mixture was evaporated to dryness in vacuo, after which 100 ml of 1 N hydrochloric acid were added. After filtrating the m-chlorobenzoic acid the filtrate was brought to pH 10 with concentrated ammonia. The desoxohydrocinchonicine-N-oxide was extracted three times with 100 ml of chloroform, after which the compound was obtained as an oil after evaporation to dryness in vacuo.

The resulting product was dissolved in 75 ml of chloroform, after which 16.2 phosphorus oxychloride, dissolved in 50 ml chloroform, were added. The mixture was refluxed for 1.5 hours, during which gaseous hydrochloric acid escaped. The reaction mixture was then cooled and poured onto a mixture of concentrated ammonia and ice. The formed 2'-chloro-desoxo-hydrocinchonicine was extracted three times with 100 ml of chloroform. The crude product was purified with column chromatography (silica gel/chloroform). After evaporation to dryness in vacuo the 2'-chloro-desoxo-hydrocinchonicine was obtained as an oil.

The obtained product was dissolved in 100 ml of 4 N sulphuric acid. The reaction mixture was refluxed for 4 hours and the conversion was followed by thin layer chromatography. After it was found that the starting product was substantially completely converted, the mixture was cooled and poured onto a mixture of concentrated ammonia and ice. The organic material was extracted three times with 100 ml of chloroform at pH 10. After purification by column chromatography (silica gel/chloroform-methanol 10:1) and evaporation to dryness the 2'-hydroxy-desoxo-hydrocinchonicine was obtained as an oil. The oil was dissolved in 50 ml of methyl ethyl ketone, to which an equivalent amount of oxalic acid was added. After crystallization and recrystallization the 2'-hydroxy-desoxo-hydrocinchonicine bioxalate was obtained. Melting point 198°–200° C.

EXAMPLE 17

2'-Hydroxy-desoxo-hydroquinicine.bioxalate (intermediate)

In the same way as described in Example 6 the title compound was prepared starting with desoxo-hydroquinicine. The melting point of the bioxalate was 196°–198° C.

EXAMPLE 18

1-(2-Trifluoromethyl-4-quinolyl)-3-[3(R)-ethyl-4(S)-piperidyl]-propanone-2-bifumarate (intermediate)

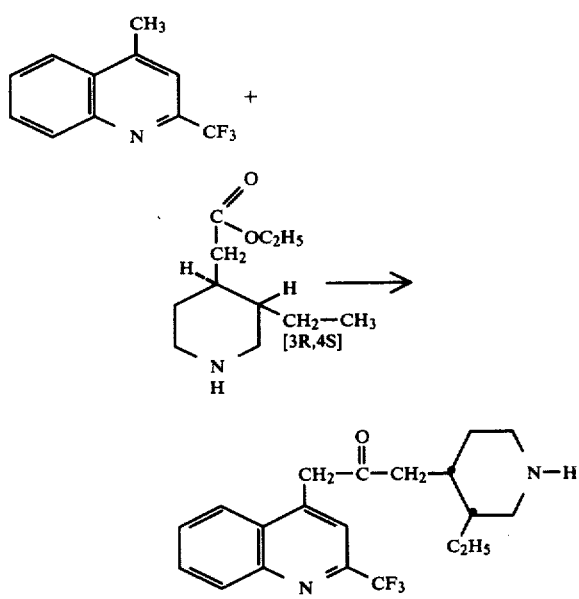

To 75 ml (124.2 mmol) of 15% n-butyllithium in hexane at −70° C. 21 ml (123 mmol) of diisopropylamine were added in 20 minutes with stirring and in a nitrogen atmosphere. Then 23.6 g (111.8 mmol) of 4-methyl-2-trifluoromethylquinoline in 80 ml of tetrahydrofuran were added in 45 minutes at −70° C. followed bij 14.5 g (72.9 mmol) of [3(R)-ethyl-4(S)-piperidyl]-acetic acid ethyl ester in 80 ml of tetrahydrofuran in 30 minutes. The reaction mixture was stirred for 2 hours at −70° C. and for 3 hours at −25° C. The reaction mixture was acidified with acetic acid to pH 6, after which 8.5 g of potassium bicarbonate were added. Then the reaction mixture was kept over night at room temperature.

The reaction mixture was diluted with 150 ml of methanol, filtered and evaporated to dryness in vacuo. To the residue 200 ml of water and 4 N hydrochloric acid were added to pH 4. Subsequently the mixture was extracted with ether (total amount 500 ml).

The water phase was made alkaline with concentrated ammonia to pH 8–9 and extracted with chloroform (total amount 300 ml). The chloroform extract was dried over magnesium sulphate, filtered and evaporated to dryness in vacuo.

The resulting crude 1-(2-trifluoromethyl-4-quinolyl)-3-[3-(R)-ethyl-4(S)-piperidyl]-propanone-2 was purified with the aid of HPLC (Silica Gel with chloroform:acetone:diethylamine 5:4:1). The yield of pure product (oil) was 44.5%. The base was converted with fumaric acid to the bifumarate (mol. ratio 1:1) with a melting point of 140° C.

EXAMPLE 19

1-(2-Methoxy-4-quinolyl)-3-[3(R)-ethyl-4(S)-piperidyl]-propanone-2 (intermediate)

In the same way as described in Example 8, but starting with 2-methoxy-4-methylquinoline in stead of 4-methyl-2-trifluoromethylquinoline, the title compound was obtained as an oil.

EXAMPLE 20

2'-Hydroxy-hydrocinchonicinol-2 (intermediate)

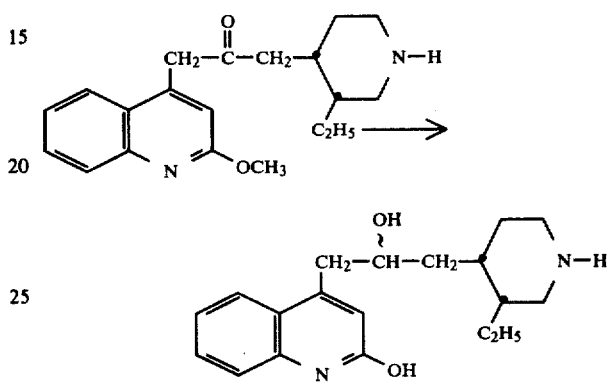

A mixture of 1.0 g (3.1 mmol) of 1-(2-methoxy-4-quinolyl)-3[3(R)-ethyl-4(S)-piperidyl]-propanone-2 (Example 19) in 10 ml of 47% HBr-solution was warmed at 105° C. for 3 hours.

After cooling to room temperature the reaction mixture was basified (pH 9) with concentrated ammonia and extracted with chloroform. The chloroform extract was dried over magnesium sulphate, filtered and evaporated in vacuo. The obtained crude 1-(2-hydroxy-4-quinolyl)-3[3(R)-ethyl-4(S)-piperidyl]-propanone-2 was reduced to the title compound in the same way as described in Example 7. The compound was obtained as an oil.

EXAMPLE 21

2'-Trifluoromethyl-hydrocinchonicinol-2.bifumarate (intermediate)

In the same way as described in Example 7 but starting with 1-(2-trifluoromethyl-4-quinolyl)-3-[3(R)-ethyl-3(S)-piperidyl]-propanone-2 (Example 18) in stead of 2'-propyl-hydrocinchonicine the title compound was prepared as a mixture of two stereoisomers. By means of column chromatography with silica gel and chloroform/methanol/diethylamine (80:5:10) as eluent these isomers were separated and both converted to their bifumarate salts with 1 equivalent of fumaric acid.

One isomer had a melting point of 149°–150° C. and the other or 190°–191° C.

EXAMPLE 22

2'-Trifluoromethyl-desoxo-hydrocinchonicine (intermediate)

In the same way as described in Example 12 but starting with 1-(2-trifluoromethyl-4-quinolyl)-3-[3(R)-ethyl-4(S)-piperidyl]-propanone-2 (Example 18) in stead of 2'-methyl-hydrocinchonicine the title compound was obtained as an oil.

EXAMPLE 23

2'-Methyl-hydrocinchonicine-O-methyloxime ether.bioxalate (intermediate)

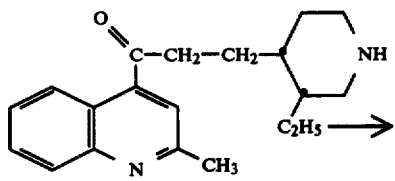

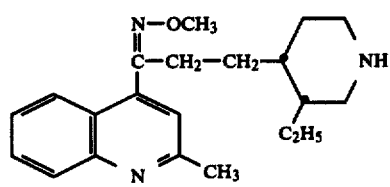

2'-Methylhydrocinchonicine (Example 1), 20 g (65 mmol) was dissolved in 200 ml of 96% alcohol, to which 7.6 g (92 mmol) of methoxylamine hydrochloride were added. The reaction mixture was refluxed for 16 hours, cooled and evaporated in vacuo. The residue was treated with 50 ml of concentrated ammonia and 100 ml of water, after which the formed product was extracted three times with 100 ml of chloroform. The chloroform fraction was evaporated in vacuo, after which the residue was dissolved in acetone. A calculated amount of oxalic acid was then added. After crystallization and recrystallization from acetone the title compound was obtained. Melting point 112°–114° C.

EXAMPLE 24

2'-Isopropyl-hydrocinchonicine-O-methyl oxime ether (intermediate)

In the same way as described in Example 23 but starting with 2'-isopropyl-hydrocinchonicine (Example 5), the title compound was obtained as an oil.

EXAMPLE 25

N-(3-benzoylpropyl)-2'-methyl-hydrocinchonicine.-bifumarate

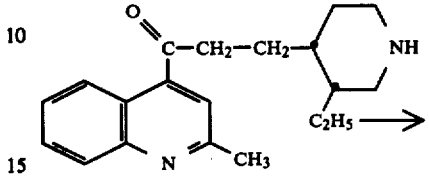

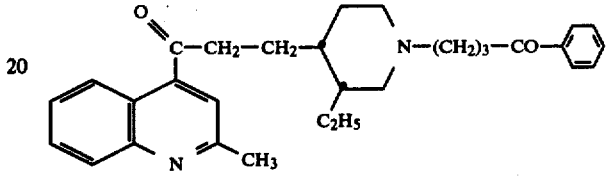

2'-Methylhydrocinchonicine (base), 17 g (55 mmol) (Example 1) was dissolved with stirring in 100 ml of dimethyl formamide, after which 12.7 g (70 mmol) of γ-chlorobutyrophenone and 12 g (120 mmol) of potassium bicarbonate were added. The mixture was heated at a temperature of 110°–120° C. for 20 hours in a nitrogen atmosphere. After the conversion was found to be substantially completed with thin layer chromatography, the reaction mixture was cooled to room temperature, after which water was added. The layers were separated and the toluene layer was evaporated in vacuo. Then 100 ml of 4 N hydrochloric acid were added, through which the compound was removed from the toluene fraction and the excess of γ-chlorobutyrophenone remained in this fraction. The water layer was made alkaline to pH 8 with 4 N sodium hydroxide, from which the free base was then extracted with 100 ml of ether. After the ether fraction was dried over molecular sieves the crude product was purified by column chromatography (silica gel/chloroform). The resulting fractions were collected and evaporated to dryness in vacuo, after which the residue was dissolved in 100 ml of methyl ethyl ketone. Then 2 g of fumaric acid was added while heating. After cooling the desired product crystallized as its bifumarate, after which it was recrystallized from methyl ethyl ketone. The melting point of the bifumarate mentioned in the title is 71°–74° C.

In the same way were prepared:

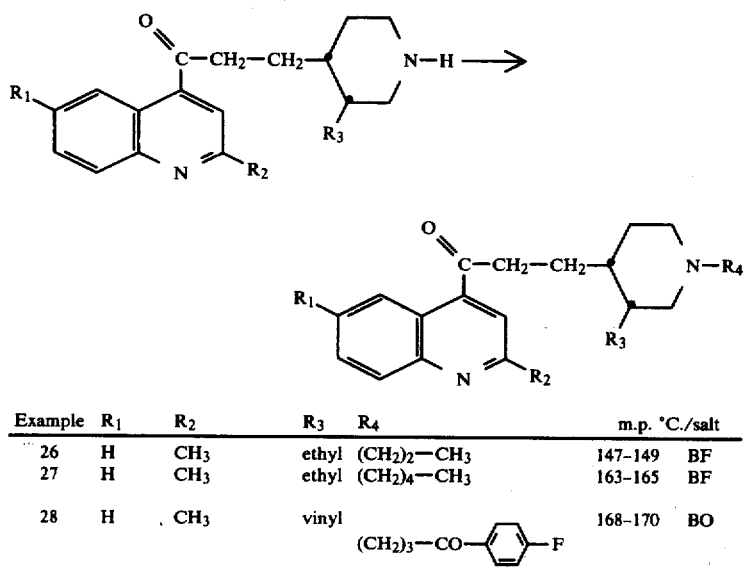

| Example | R₁ | R₂ | R₃ | R₄ | m.p. °C./salt | |
|---|---|---|---|---|---|---|
| 26 | H | CH₃ | ethyl | (CH₂)₂—CH₃ | 147–149 | BF |
| 27 | H | CH₃ | ethyl | (CH₂)₄—CH₃ | 163–165 | BF |
| 28 | H | CH₃ | vinyl | (CH₂)₃—CO—C₆H₄—F | 168–170 | BO |
| 29 | OCH₃ | CH₃ | ethyl | (CH₂)₂—CH₃ | 224 | HCl |
| 30 | H | (CH₂)₂—CH₃ | ethyl | (CH₂)₂—CH₃ | 130 | O |
| 31 | H | (CH₂)₂—CH₃ | ethyl | (CH₂)₄—CH₃ | 140–143 | BO |
| 32 | H | (CH₂)₂—CH₃ | ethyl | (CH₂)₃—CO—C₆H₅ | 127–131 | TO |
| 33 | H | (CH₂)₂—CH₃ | ethyl | CH₂—CH₂—C≡CH | 185–187 | BO |
| 34 | H | (CH₂)₂—CH₃ | ethyl | (CH₂)₄—OCH₃ | 156–158 | BO |
| 35 | H | (CH₂)₂—CH₃ | ethyl | (CH₂)₄—CN | 138 | BO |

BF = bifumarate (1:1)
BO = bioxalate (1:1)
O = oxalate (2:1)
TO = tetraoxalate (1:2)

EXAMPLE 36

N-(2-hydroxy-2-methylpropyl)-2′-isopropylhydrocinchonicine.bioxalate

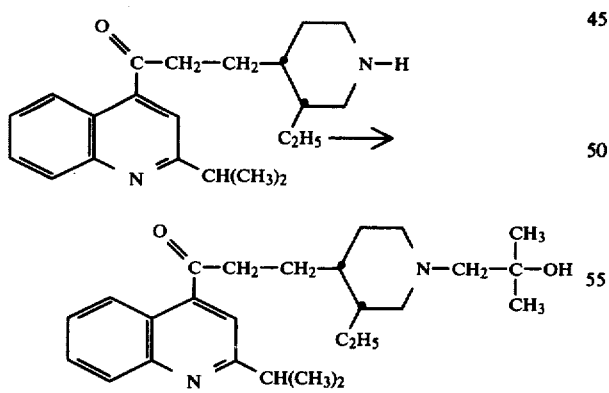

A mixture of 10.0 g (30 mmol) of 2′-isopropylhydrocinchonicine (Example V) and 3.25 g (45 mmol) of 1,2-epoxy-2-methylpropane in 100 ml of absolute ethanol was warmed at 60° C. for 6 hours.

After cooling to room temperature the reaction mixture was evaporated to dryness in vacuo. The obtained crude product was purified by column chromatography (silica gel/chloroform). The yield of pure base was 9.0 g (oil). The base was converted to its bioxalate salt having a melting point of 135° C.

EXAMPLE 37

N-(3-benzoylpropyl)-2′-propyl-hydroconchonicinol-1.bioxalate

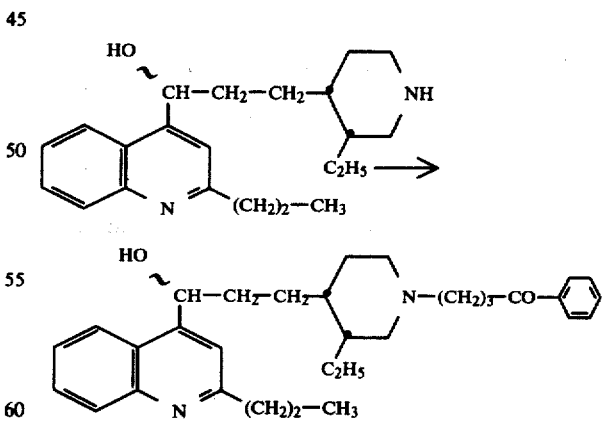

2′-Propyl-hydrocinchonicinol-1 (Example 7), 10 g (29 mmol), was dissolved in 100 ml of toluene/methyl ethyl ketone (1:1), after which 9.2 g (50 mmol) of γ-chlorobutyrophenone and 10 g (100 mmol) of potassium bicarbonate were added. The reaction was refluxed for 24 hours and the conversion was followed by thin layer chromatography. After a substantially complete conversion was found, the mixture was worked up in the same way as described in the previous examples. After purification of the crude product by column chromatography (silical gel/chloroform) the title compound was obtained after evaporation in vacuo as a base, which was then converted with oxalic acid to the oxalate. The salt was recrystallized from acetone.

Melting point of the title compound 106°-110° C.

In the same way were prepared:

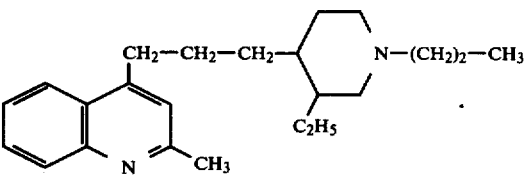

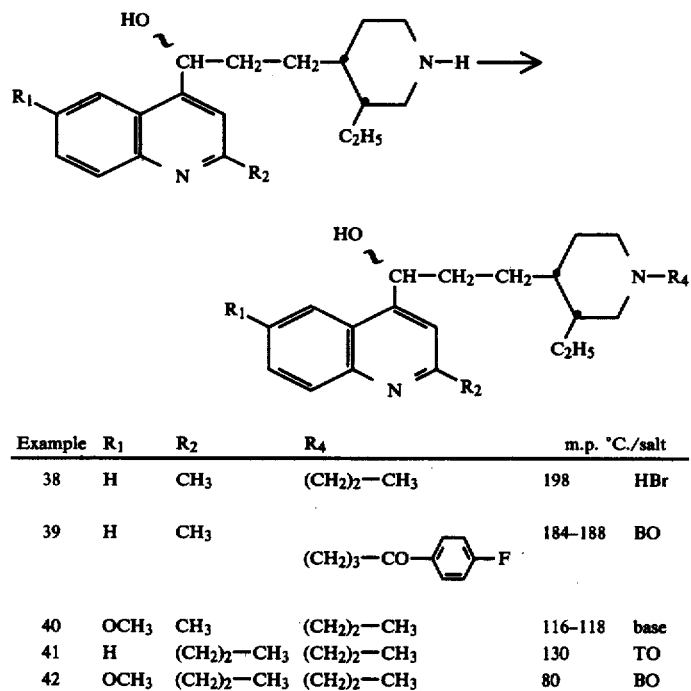

| Example | R₁ | R₂ | R₄ | m.p. °C./salt | |
|---|---|---|---|---|---|
| 38 | H | CH₃ | (CH₂)₂—CH₃ | 198 | HBr |
| 39 | H | CH₃ | (CH₂)₃—CO—C₆H₄—F | 184-188 | BO |
| 40 | OCH₃ | CH₃ | (CH₂)₂—CH₃ | 116-118 | base |
| 41 | H | (CH₂)₂—CH₃ | (CH₂)₂—CH₃ | 130 | TO |
| 42 | OCH₃ | (CH₂)₂—CH₃ | (CH₂)₂—CH₃ | 80 | BO |

BO = bioxalate (mol. ratio 1:1)
TO = tetraoxalate (mol. ratio 1:2)

EXAMPLE 43

2'-Methyl-N-propyl-desoxo-hydrocinchonicine.bioxalate

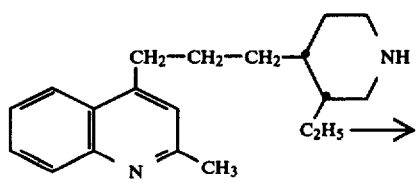

2'-Methyl-desoxo-hydrocinchonicine (Example 12), 13.5 g (35 mmol), was dissolved in 100 ml of dimethyl formamide, after which 4.9 g (40 mmol) of propyl bromide and 8 g (80 mmol) of potassium bicarbonate were added. This mixture was heated at 70°-80° C. for 1.5 hours while stirring. After it was found with thin layer chromatography that the conversion was complete, the reaction mixture was evaporated in vacuo. The reaction product was extracted with chloroform and purified by column chromatography (silica gel/chloroform). The resulting fractions with the desired product were collected and evaporated in vacuo. The residue was dissolved in 50 ml of methyl ethyl ketone, after which 4 g of oxalic acid were added while heating. The bioxalate of the title compound crystallized, after which the isolated compound was recrystallized from acetone-methylalcohol. Melting point of the bioxalate 158°-160° C.

In the same way were prepared:

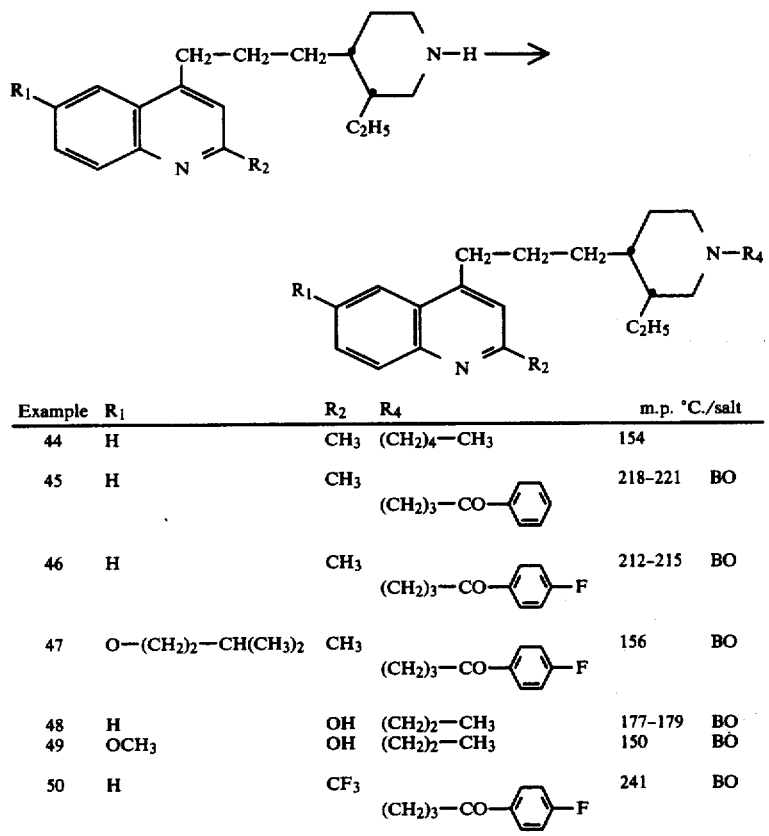

| Example | R₁ | R₂ | R₄ | m.p. °C./salt | |
|---|---|---|---|---|---|
| 44 | H | CH₃ | (CH₂)₄—CH₃ | 154 | |
| 45 | H | CH₃ | (CH₂)₃—CO—C₆H₅ | 218–221 | BO |
| 46 | H | CH₃ | (CH₂)₃—CO—C₆H₄—F | 212–215 | BO |
| 47 | O—(CH₂)₂—CH(CH₃)₂ | CH₃ | (CH₂)₃—CO—C₆H₄—F | 156 | BO |
| 48 | H | OH | (CH₂)₂—CH₃ | 177–179 | BO |
| 49 | OCH₃ | OH | (CH₂)₂—CH₃ | 150 | BO |
| 50 | H | CF₃ | (CH₂)₃—CO—C₆H₄—F | 241 | BO |

BF = bifumarate (mol. ratio 1:1)
BO = bioxalate (mol. ratio 1:1)

EXAMPLE 51

N-methyl-2'-propoxy-hydrocinchonicine.bioxalate

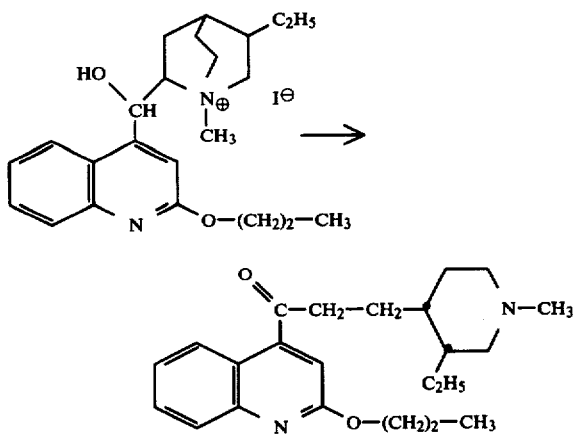

2'-Propoxy-epi-hydrocinchonidine-methiodide, 11 g (22 mmol), was dissolved in 55 ml of 96% ethylalcohol, to which 110 ml of a 10% potassium hydroxide solution in water were added. The mixture was refluxed for 1 hour and the conversion was followed by thin layer chromatography. After a complete conversion was found, the mixture was evaporated in vacuo and extracted twice with 100 ml of toluene. The toluene extract was washed twice with 100 ml of water and dried over magnesium sulphate. After evaporation of the toluene fraction the crude product was purified by column chromatography (silica gel/ethyl acetate) and the mixture was evaporated in vacuo. The resulting crude N-methyl-2'-propoxy-hydrocinchonicine was dissolved in acetone and an equivalent amount of oxalic acid was added. After crystallization and recrystallization the title compound was obtained with a melting point of 138°–141° C.

EXAMPLE 52

2'-Methoxy-N-methyl-hydrocinchonicine.bioxalate

In the same way as described in Example 51, but starting with 2'-methoxy-epi-hydrocinchonidine-methiodide the title compound was prepared. Melting point of the bioxalate 187° C.

EXAMPLE 53

2'-Methoxy-N-propyl-hydrocinchonicinol-2.hydrochloride

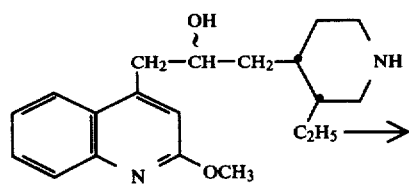

-continued

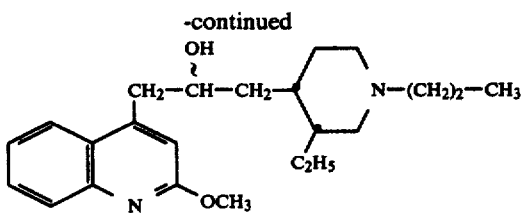

2'-Methoxy-hydrocinchonicinol-2 (Example 14), 3.3 g (10 mmol), was dissolved in 35 ml of methyl isobutyl ketone, after which 100 mg of potassium iodide, 1.35 g of propylbromide, 2.1 g of sodium carbonate and 25 ml of dimethyl formamide were added. The mixture was heated at 80° C. for 1 hour, after which the conversion was found substantially complete with the aid of thin layer chromatography. The reaction mixture was then poured into 100 ml of water and extracted twice with 50 ml of ethyl acetate. The collected ethyl acetate fractions were dried over magnesium sulphate, filtered and evaporated in vacuo, affording the crude product as an oil. This was then purified by column chromatography (silica gel/chloroform). The resulting solution was evaporated to dryness in vacuo, after which the residue was dissolved in acetone while heating. An equivalent amount of hydrochloric acid, dissolved in isopropylalcohol, was then added and the title compound crystallized as the hydrochloride. Melting point 158°–160° C.

In the same way were obtained:

EXAMPLE 62

N-(2-Hydroxy-2-methylpropyl)-2'-methoxyhydrocinchonicinol-2

In the same way as described in Example 36 2'-methoxy-hydrocinchonicinol-2 (Example 14) was converted into the title compound.

The melting point of the base was 105°–108° C.

EXAMPLE 63

1-(2-Methoxy-4-quinolyl)-3-[3(R)-ethyl-N-propyl-4(S)-piperidyl]-propanone-2.bioxalate In the same way as described in Example 25 1-(2-methoxy-4-quinolyl)-3-[3(R)-ethyl-4(S)-piperidyl]-propanone-2 (Example 19) was converted with propylbromide into the title compound. The melting point of the bioxalate was 138°–139° C.

EXAMPLE 64

1-(2-Trifluoromethyl-4-quinolyl)-3-[3(R)-ethyl-N-pentyl-4(S)-piperidyl]-propanone-2.bifumarate In the same way as described in Example 25 1(2-trifluoromethyl-4-quinolyl)-3-[3(R)-ethyl-4(S)-piperidyl]-propanone-2 (Example 18) was converted with pentylbromide into the title compound. The melting point of the bifumarate was 160° C.

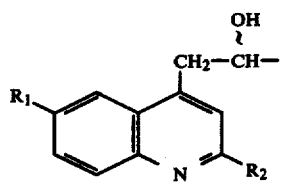

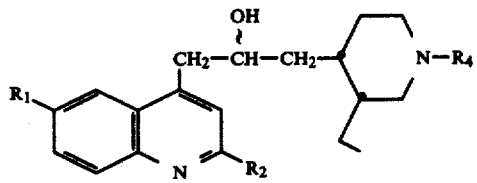

| Example | R₁ | R₂ | R₄ | m.p. °C. | salt |
|---|---|---|---|---|---|
| 54 | H | OCH₃ | (CH₂)₃—CO—Ph | 194–196 | BO |
| 55 | H | OCH₃ | (CH₂)₃—CH[—C₆H₄—F]₂ | 116–120 | TF |
| 56 | OCH₃ | OCH₃ | (CH₂)₂—CH₃ | 181–183 | BO |
| 57 | H | OH | (CH₂)₂—CH₃ | 213–214 | HBr |
| 58 | H | CF₃ | (CH₂)₂—CH₃ | 186–187 | BO (mixture of isomers) |
| 59 | H | CF₃ | (CH₂)₂—CH₃ | 204 | BO (first isomer) |
| 60 | H | CF₃ | (CH₂)₂—CH₃ | 113–115 | BO (second isomer) |
| 61 | H | CF₃ | (CH₂)₄—CH₃ | 120 | BO |

BO = bioxalate (mol. ratio 1:1)
TF = trifumarate (mol. ratio 2:3)

EXAMPLE 65

N-[3-(4-Fluorobenzoyl)propyl]-2'-isopropylhydrocinchonicine-O-methyl oxime ether.dihydrochloride In the same way as described in Example 25 2'-isopropyl-hydrocinchonicine-O-methyl oxime ether (Example 24) was converted into the title compound with γ-chloro-4-fluorobutyrophenone. The melting point of the dihydrochloride was 130° C.

EXAMPLE 66

N-(2-Hydroxy-2-methylpropyl)-2'-methyl-hydrocinchonicine-O-methyl oxime ether.bioxalate In the same way as described in Example 36, but starting with 2'-methyl-hydrocinchonicine-O-methyl oxime ether (Example 23) the title compound was obtained.

The melting point of the bioxalate was 130°–134° C.

EXAMPLE 67

2'-Methyl-N-propyl-hydrocinchonicinol-1.hydrobromide

In the same way as described in Example 7 2'-methyl-N-propyl-hydrocinchonicine (Example 26) was converted into the title compound.

The hydrobromide had a melting point of 198° C.

EXAMPLE 68

2'-Methyl-N-propyl-desoxo-hydrocinchonicine.bioxalate

In the same way as described in Example 12, but starting with 2'-methyl-N-propyl-hydrocinchonicine (Example 26) the title compound was obtained. The melting point of the bioxalate was 158°–160° C.

EXAMPLE 69

1-(2-Trifluoromethyl-4-quinolyl)-3-[3(R)-ethyl-N-propyl-4(S)-piperidyl]-propanol-2-methyliodide (first isomer)

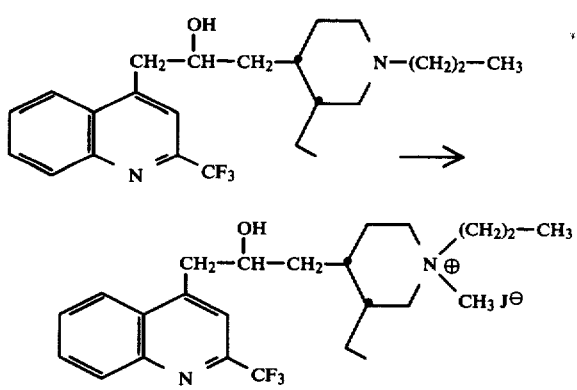

A mixture of 3.7 g (9.1 mmol) of 1-(2-trifluoromethyl-4-quinolyl)-3-[3(R)-ethyl-N-propyl-4(S)-piperidyl]-propanol-2 (first isomer, Example 59) and 3.5 ml of methyliodide in 25 ml of acetone was stirred for 1.5 hours at room temperature. The first crop of the desired product crystallized and was filtered off. Evaporation of the filtrate yielded a second crop of product. After recrystallization from a mixture of ethylacetate and methanol the total yield was 2.2 g. Melting point 132° C.

EXAMPLE 70

N-Cyclohexyl-2'-methyl-desoxo-hydrocinchonicine

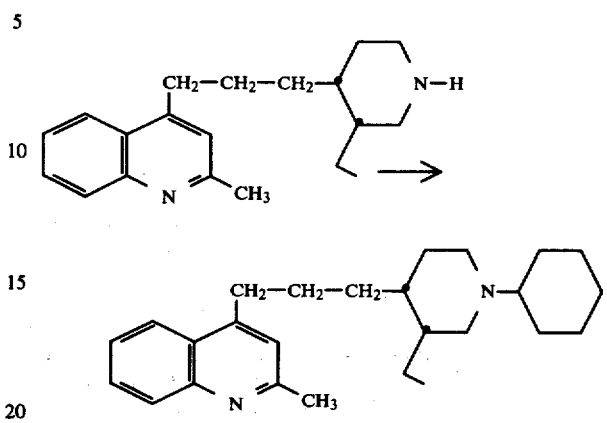

To a solution of 6.7 g (26.0 mmol) of 2'-methyl-desoxo-hydrocinchonicine (Example 12) in 50 ml of methanol was added 0,6 g of potassium hydroxide with stirring. After dissolution, 2.3 g (26.0 mmol) of cyclohexanone were added with stirring, followed by 3.0 g (48.0 mmol) of sodium cyanoborohydride. After stirring for 30 minutes at room temperature another 0.6 g of potassium hydroxide was added and stirring was continued for 6 hours.

After evaporation of the methanol under reduced pressure, water was added to the residue and acidified with 4 N hydrochloric acid. After extraction with ether, the water layer was basified with 4 N sodium hydroxide solution and extracted with ethylacetate. The ethylacetate extract was dried over magnesium sulphate, filtered and evaporated to dryness in vacuo. The residue was purified by means of column chromatography with silica gel and ethylacetate: diethylamine (9:1) as the eluent. The title compound was obtined as an oil.

EXAMPLE 71

N-(2-hydroxy-2-methylpropyl)-2'-methyl-hydrocinchonicine-O-methyl oxime ether.bioxalate In the same way as described in Example 36 2'-methyl-hydrocinchonicine was converted into N-(2-hydroxy-2-methylpropyl)-2'-methyl-hydrocinchonicine. This compound was obtained as an oil.

In the same manner as described in Example 23 the above prepared compared was converted into the title compound. The bioxalate had a melting point of 130°–134° C.

PHARMACOLOGY

Experiment 1-Effectiveness of the compounds of Examples in spontaneously hypertensive rats Systolic blood pressures were recorded by a modification of the tail cuff method described by I.M. Claxton et al., Eur. J.Pharmacology 37, 179 (1976). An oscilloscope or W+W BP recorder, model 8002, was used to display pulses.

Prior to all measurements rats were placed in a heated environment (33.5±0.5° C.) before transfer to a restraining cage. Each determination of blood pressure was the mean of at least 6 readings.

Spontaneously hypertensive rats (aged 12-18 weeks) with systolic blood pressures >170 mm Hg were considered hypertensive.

In the following table the results with certain compounds of the invention, which have been carried out with the above-described method, are mentioned. The numbers of the compounds correspond with those of the Examples.

| Compound No. | Dosage mg/kg | Change of systolic blood-pressures (%) in different time intervals (h) | | | | |
|---|---|---|---|---|---|---|
| | | 1 | 2 | 4 | 6 | 24 |
| 25 | 100 | −16 | −25 | −9 | −5 | +2 |
| 26 | 10 | 0 | +3 | −5 | −7 | — |
| 27 | 100 | −1 | −13 | −28 | −16 | −3 |
| 28 | 10 | −5 | −2 | −10 | −11 | +5 |
| 29 | 100 | −10 | −27 | −18 | −22 | 0 |
| 32 | 10 | −4 | −11 | −8 | −22 | −3 |
| 38 | 10 | +1 | 0 | −3 | −4 | 0 |
| 39 | 1 | −16 | −24 | −26 | −23 | −1 |
| 41 | 10 | −6 | −11 | −15 | −17 | +3 |
| 43 | 100 | −1 | −12 | −28 | no pulses | −15 |
| 44 | 100 | +2 | −15 | −30 | −43 | −6 |
| 45 | 10 | −14 | −6 | −14 | −21 | −2 |
| 46 | 10 | −22 | −24 | −20 | −20 | −1 |
| 47 | 10 | −26 | −21 | −30 | −22 | 0 |
| 50 | 10 | −4 | −16 | −16 | −13 | — |
| 51 | 3 | −1 | 0 | −7 | −13 | −1 |
| 53 | 10 | −4 | −5 | −11 | −3 | — |
| 54 | 10 | −17 | −1 | −16 | −16 | +7 |
| 55 | 10 | −11 | −5 | −7 | −10 | −2 |
| 61 | 10 | −8 | −10 | −13 | −12 | −7 |
| 63 | 10 | −1 | +1 | −4 | −3 | −6 |
| 64 | 100 | −5 | −23 | −17 | −13 | −8 |

Experiment 2-Effectiveness of the compounds of Examples in the Guinea Pigs Electrostimulation Test Arrhythmias are induced in guinea pigs by electrostimulation of the right ventricle of the heart. The animals are anaesthesized with urethane (1.2 g/kg i.p.) and artificially respirated before a needle electrode is inserted in the right ventricle of the heart. Substances are given intraduodinally 30 minutes before the stimulation at a standard dose of 32 mg/kg. In some cases a different dose was used as indicated.

The voltage needed for induction of extra systoles in control animals (n=6) is compared with that required for induction of arrhythmias in treated animals (n=6).

This method is based on the work of L. Szekeres and G. J. Papp, Naunyn-Schmiedebergs Arch. Exp. Path. Pharmak., 245, 70 (1963).

In the table the results of certain compounds of the invention are mentioned, which have been carried out according to the method described above.

The numbers of the compounds correspond with those of the Examples.

| Compound No. | Percent increase in voltage required for arrhythmia |
|---|---|
| 25 | 5 |
| 26 | 24 |
| 27 | −2 |
| 29 | 9 (at 16 mg/kg) |
| 30 | 60 (at 8 mg/kg) |
| 31 | 31 |
| 32 | 52 |
| 36 | 91 |
| 38 | 31 (at 16 mg/kg) |
| 39 | 5 |
| 40 | 44 (at 16 mg/kg) |
| 41 | 101 (at 8 mg/kg) |
| 42 | 74 (at 16 mg/kg) |
| 43 | 9 |
| 48 | 19 (at 16 mg/kg) |
| 49 | 21 (at 16 mg/kg) |
| 51 | −5 |
| 52 | 25 (at 8 mg/kg) |
| 53 | 28 (at 8 mg/kg) |
| 54 | 16 |
| 56 | 112 (at 20 mg/kg) |
| 58 | 133 (at 10 mg/kg) |
| 59 | 55 (at 4 mg/kg) |
| 60 | 137 (at 8 mg/kg) |
| 61 | 11 (at 8 mg/kg) |
| 63 | 12 (at 4 mg/kg) |
| 66 | 43 (at 16 mg/kg) |

The compounds did not cause signs of toxicity at the doses used in the described tests. The LD$_{50}$ in mice of the compound N-(n-propyl)-2'-methyl-hydrocinchonicine was found to be 500 mg/kg.

We claim:

1. A compound of formula 1, or a salt thereof,

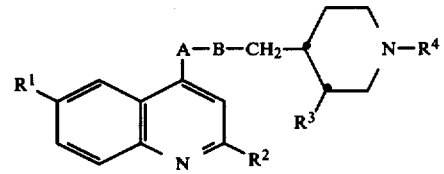

in which
A—B is —CH$_2$—CH$_2$—, —CHOH—CH$_2$—, —CH$_2$—CHOH—, —C(O)—CH$_2$—, —CH$_2$—C(O)—, —C(NOR$^5$)—CH$_2$—or —CH$_2$—C(NOR$^5$)—,
R$^1$ is hydrogen, hydroxy or lower alkoxy,
R$^2$ is lower alkyl, hydroxy, lower alkoxy, or CF$_3$,
R$^3$ is ethyl or vinyl,
R$^4$ is C$_{1-9}$ alkyl, C$_{2-9}$ hydroxyalkyl or lower alkoxyalkyl, C$_{5-6}$ cycloalkyl, C$_{3-6}$ cycloalkyl lower alkyl, cyano lower alkyl, lower alkenyl, lower alkynyl, tetrahydrofurfuryl, mono- or di-lower alkylamino lower alkyl; mono- or di-lower alkylamino lower hydroxyalkyl; phenyl C$_{1-4}$ alkyl, phenyl C$_{1-4}$ hydroxyalkyl, diphenyl C$_{1-4}$ alkyl, or benzoyl C$_{1-4}$ alkyl, in which the phenyl moiety is unsubstituted or substituted by one substituent selected from halogen, lower alkyl or lower alkoxy; furyl C$_{1-4}$ alkyl, thienyl C$_{1-4}$ alkyl, furoyl C$_{1-4}$ alkyl or thienoyl C$_{1-4}$ alkyl, and
R$^5$ is lower alkyl,
whereby the substituents at the 3- and 4-positions of the piperidine ring are in the cis-configuration.

2. A compound of claim 1, as represented by formula 1n

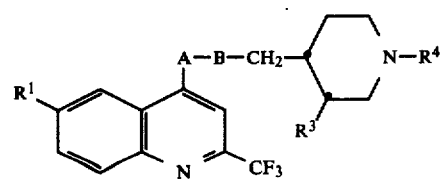

in which A—B, R$^1$, R$^3$ and R$^4$ are as defined in claim 1.

3. A compound of claim 1, as represented by formula 1c

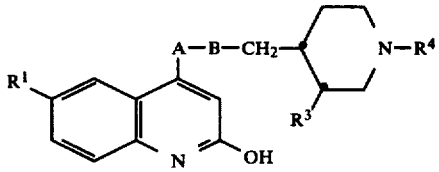

in which A—B, $R^1$, $R^3$ and $R^4$ are as defined in claim 1.

4. A compound of claim 1, as represented by formula 1e

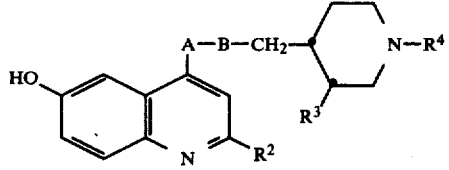

in which A—B, $R^2$, $R^3$ and $R^4$ are as defined in claim 1.

5. A compound of claim 1, as represented by formula 1o

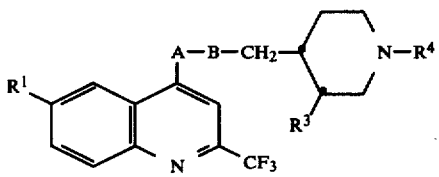

in which A—B is —CHOH—$CH_2$— and —$CH_2$—CHOH—, and $R^1$, $R^3$ and $R^4$ are as defined in claim 1.

6. A compound of claim 1, as represented by formula 1p

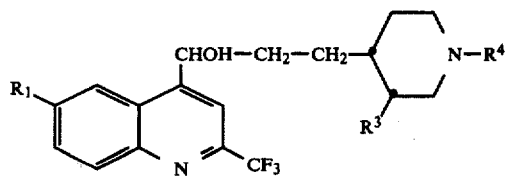

in which $R^4$ is alkyl or alkoxyalkyl and $R^1$ and $R^3$ are as defined in claim 1.

7. A compound of claim 1, as represented by formula 1q

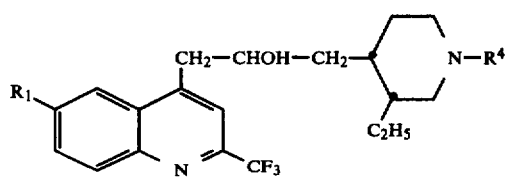

in which $R^1$ is hydrogen or methoxy, and $R^3$ is ethyl and $R^4$ is n-propyl, n-butyl or n-pentyl.

8. A compound of claim 1, as represented by formula 1r

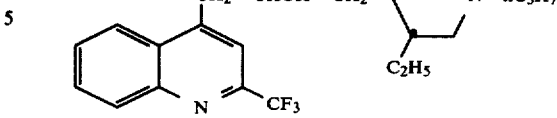

the mixture of diastereoisomers as well as the separated diastereoisomers.

9. A compound of claim 1, as represented by formula 1g,

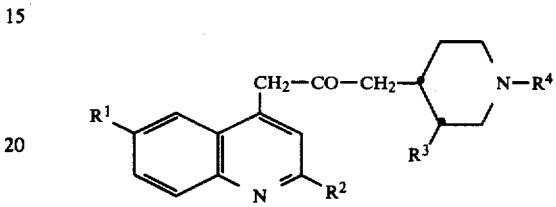

in which $R^1$, $R^2$, $R^3$ and $R^4$ are as defined in claim 1, and the O-alkyloxime ethers of such a compound 10. A compound of claim 1, as represented by formula 1h,

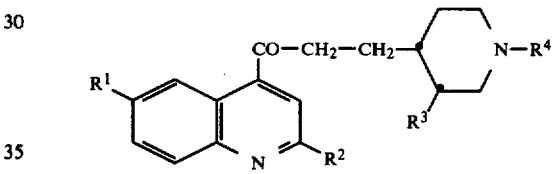

in which $R^1$, $R^2$, $R^3$ and $R^4$ are as defined in claim 1, and the O-alkyloxime ethers of such a compound.

11. A compound according to claim 1 in which A—B is —C(O)—$CH_2$—, $R^1$ is hydrogen, $R^2$ is n-propyl, $R^3$ is ethyl and $R^4$ is n-propyl, n-pentyl or 3-benzoyl-n-propyl.

12. A compound according to claim 1 in which A—B is —$CH_2$—$CH_2$—, $R^1$ is hydrogen, $R^2$ is methyl, $R^3$ is ethyl and $R^4$ is 3-benzoyl-n-propyl or 3-(4-fluorobenzoyl)-n-propyl.

13. A compound according to claim 1 in which A—B is —$CH_2$—$CH_2$—, $R^1$ is isopentoxy, $R^2$ is methyl, $R^3$ is ethyl and $R^4$ is 3-(4-fluorobenzoyl)-n-propyl.

14. A compound according to claim 1 in which A—B is —C(NOR$^5$)—$CH_2$—, $R^1$ is hydrogen, $R^2$ is methyl, $R^3$ is ethyl and $R^4$ is (2-hydroxy-2-methyl)-n-propyl.

15. A compound according to claim 1 in which A—B is —CHOH—$CH_2$—, $R^1$ is hydrogen, $R^2$ is methyl, $R^3$ is ethyl and $R^4$ is 3-(4-fluorobenzoyl)-n-propyl.

16. A compound according to claim 1 in which A—B is —CHOH—$CH_2$—, $R^2$ is methyl, $R^3$ is ethyl, $R^4$ is n-propyl and $R^1$ is hydrogen or methoxy.

17. A compound according to claim 1 in which A—B is —C(O)—$CH_2$, $R^1$ is hydrogen, $R^2$ is isopropyl, $R^3$ is ethyl and $R^4$ is (2-hydroxy-2-methyl)-n-propyl.

18. A compound according to claim 1 in which A—B is —$CH_2$—CHOH—, $R^1$ is hydrogen, $R^2$ is methoxy, $R^3$ is ethyl and $R^4$ is n-propyl or 3-benzoyl-n-propyl.

19. A pharmaceutical composition comprising a cardiovascularly effective amount of a compound according to claim 1, or a pharmaceutically acceptable salt thereof, in combination with a pharmaceutically acceptable carrier.

20. The method of treating cardiovascular conditions in a human or other animal in need thereof which comprises administering an effective amount of a compound according to claim 1.

21. A compound according to claim 1, wherein $R^2$ is lower alkyl, hydroxy or lower alkoxy.

22. A compound according to claim 1, wherein $R^2$ is lower alkyl.

23. A compound according to claim 1, wherein $R^2$ is alkyl and $R^4$ is benzoyl $C_{1-4}$ alkyl in which the phenyl moiety is unsubstituted or substituted by one substituent selected from halogen, lower alkyl or lower alkoxy.

24. A compound according to claim 1, wherein $R^2$ is lower alkoxy.

25. A compound according to claim 1, wherein —A—B— is —CHOH—CH$_2$— or —CH$_2$—CHOH—.

26. A compound according to claim 1, wherein $R^4$ is benzoylalkyl in which the phenyl moiety is unsubstituted or substituted by one substituent selected from halogen, lower alkyl or lower alkoxy.

27. A compound according to claim 1, wherein —A—B— is —CH$_2$—CH$_2$—CH$_2$—.

28. A compound according to claim 1, wherein $R^2$ is lower alkyl and $R^4$ is benzoyl $C_{1-4}$ alkyl in which the phenyl moiety is unsubstituted or substituted by one substituent selected from halogen, lower alkyl or lower alkoxy.

29. A compound according to claim 1, wherein $R^4$ is $C_{2-9}$ hydroxyalkyl, lower alkoxyalkyl or cyano lower alkyl.

30. A compound according to claim 1, wherein —A—B— is —C(NOR$^5$) —CH$_2$— or —CH$_2$—C(NOR$^5$)— and $R^5$ is as defined in claim 1.

31. A compound according to claim 1, wherein —A—B— is —CHOH—CH$_2$— or —CH$_2$—CHOH—, $R^1$ is hydrogen or methoxy, $R^2$ is lower alkoxy, lower alkyl or hydroxy, $R^3$ is ethyl and $R^4$ is lower alkyl, lower hydroxyalkyl or lower alkoxy-lower alkyl.

* * * * *